US012589146B2

(12) United States Patent
Wright et al.

(10) Patent No.: US 12,589,146 B2
(45) Date of Patent: Mar. 31, 2026

(54) ADJUVANTED PROTEIN VACCINES COMPRISING MODIFIED FULL-LENGTH SPIKE PROTEIN OF SARS-CoV-2 COMPOSITION AND METHODS OF USE

(71) Applicant: D4 Labs, LLC, Pacific Grove, CA (US)

(72) Inventors: David Craig Wright, Pacific Grove, CA (US); Michael Bowe, Marina, CA (US); Emily Wright, Covina, CA (US); Peter Pushko, Frederick, MD (US)

(73) Assignee: D4 Labs, LLC, Pacific Grove, CA (US)

( * ) Notice: Subject to any disclaimer, the term of this patent is extended or adjusted under 35 U.S.C. 154(b) by 0 days.

(21) Appl. No.: 18/172,966

(22) Filed: Feb. 22, 2023

(65) Prior Publication Data

US 2024/0277832 A1     Aug. 22, 2024

(51) Int. Cl.

| | |
|---|---|
| *A61K 39/215* | (2006.01) |
| *A61K 39/00* | (2006.01) |
| *A61K 39/39* | (2006.01) |
| *A61P 31/14* | (2006.01) |
| *C07K 14/165* | (2006.01) |
| *C12N 7/00* | (2006.01) |

(52) U.S. Cl.
CPC ............ *A61K 39/215* (2013.01); *A61K 39/39* (2013.01); *A61P 31/14* (2018.01); *C07K 14/165* (2013.01); *C12N 7/00* (2013.01); *A61K 2039/55555* (2013.01); *A61K 2039/575* (2013.01)

(58) Field of Classification Search
None
See application file for complete search history.

(56) References Cited

U.S. PATENT DOCUMENTS

| | | | | |
|---|---|---|---|---|
| 5,665,380 A | * | 9/1997 | Wallach ................... | A61P 7/06 514/1.2 |
| 6,110,492 A | * | 8/2000 | Alving ........... | A61K 39/001186 436/829 |
| 10,787,501 B1 | | 9/2020 | Babb et al. | |
| 2010/0226932 A1 | | 9/2010 | Smith et al. | |
| 2022/0202930 A1 | | 6/2022 | Curevac et al. | |

FOREIGN PATENT DOCUMENTS

| | | |
|---|---|---|
| WO | WO 2022/137133 | 6/2022 |
| WO | WO 2022/180635 | 9/2022 |
| WO | WO 2022/221496 | 10/2022 |
| WO | WO 2022/226108 | 10/2022 |

OTHER PUBLICATIONS

Cao, et al. Nature. Feb. 2022;602(7898):657-663. doi: 10.1038/s41586-021-04385-3. Epub Dec. 23, 2021. PMID: 35016194.. (Year: 2021).*

Sulbaran, et al. Cell Rep Med. Jan. 24, 2022;3(2):100528. doi: 10.1016/j.xcrm.2022.100528. PMID: 35233549. (Year: 2022).*
International Search Report for PCT/US2022/049375, issued Jun. 14, 2023.
Lopandic et al., IgM and IgG Immunoreactivity of SARS-CoV-2 Recombinant M Protein, International Journal of Molecular Sciences, vol. 22, Iss. 4951, May 7, 2021, pp. 1-11.
Aboelwafa et al., Comparative Study on the Effects of Some Polyoxyethylene Alkyl Ether and Sorbitan Fatty Acid Ester Surfactants on the Performance of Transdermal Carvedilol Proniosomal Gel Using Experimental Design, AAPS PharmSciTech, vol. 11, No. 4, Nov. 10, 2012, pp. 1591-1602.
Ge et al., Advances of Non-Ionic Surfactant Vesicles (Niosomes) and Their Application in Drug 1-9, 12-15.
Pushko et al., Evaluation of influenza virus-like particles and Novasome adjuvant as candidate vaccine for avian influenza, Vaccine, vol. 25, Iss. 21, Mar. 9, 2017, pp. 4283-4290.
International Search Report for PCT/US2022/025622, issued Aug. 10, 2022.
Huang, W.C. et al., 'SARS-CoV-2 RBD Neutralizing Antibody Induction is Enhanced by Particulate Vaccination', Adv. Mater., 2020, vol. 32, article No. 200563, pp. 1-11.
Tandrup Schmidt, S. et al., 'Liposome-Based Adjuvants for Subunit Vaccines: Formulation Strategies for Subunit Antigens and Immunostimulators', Pharmaceutics, 2016, vol. 8, article No. 7, pp. 1-22.
Lan, J. et al., 'Structure of the SARS-CoV-2 spike receptor-binding domain bound to the ACE2 receptor', Nature, Mar. 30, 2020, vol. 58, pp. 215-220.
Ou, X. et al., 'Characterization of spike glycoprotein of SARS-CoV-2 on vims entry and its immune cross-reactivity with SARS-CoV', Nature Communications, Mar. 27, 2020, vol. 11, article No. 1620, pp. 1-12.

* cited by examiner

*Primary Examiner* — Benjamin P Blumel
*Assistant Examiner* — Jeffrey Mark Sifford
(74) *Attorney, Agent, or Firm* — King & Spalding

(57) ABSTRACT

Disclosed herein are adjuvanted protein vaccines comprising: a non-phospholipid liposome and one or more proteins, wherein the protein is encapsulated within the non-phospholipid liposome, and wherein the protein is selected from:

(i) a modified full-length spike protein that generates IgG antibody responses for 120 days after two injections of the adjuvanted protein vaccine, by subcutaneous or intramuscular routes;

(ii) a modified spike protein sequence of a coronavirus;

(iii) a protein sequence from a coronavirus; and (iv) a protein from an infectious agent that generates IgG antibody responses to proteins after one or two subcutaneous or intramuscular injections.

Also disclose herein are modified spike protein sequence containing a modified full-length SARS-COV-2 spike protein sequence. Methods of use of the vaccines and sequences are also disclosed herein.

10 Claims, 22 Drawing Sheets

Specification includes a Sequence Listing.

SVE52.SA.O.BA.1.MFLp SC Sino Omicron Antigen

Primary 1:500
Secondary 1:100

ADJUVANTED PROTEIN VACCINES COMPRISING MODIFIED FULL-LENGTH SPIKE PROTEIN OF SARS-CoV-2 COMPOSITION AND METHODS OF USE

FIELD OF THE INVENTION

Disclosed herein are adjuvanted protein vaccines, and components and methods of use thereof. The adjuvanted protein vaccines are suitable for subcutaneous or intramuscular administration. Advantageously, the adjuvanted protein vaccines can be used to generate an IgG antibody response with a single injection.

SEQUENCE LISTING

The instant application contains a Sequence Listing which has been submitted electronically in XML file format and is hereby incorporated by reference in its entirety. Said XML copy, created on Apr. 26, 2023, is named 31579_105003_WO_SL.xml and is 17,484 bytes in size.

BACKGROUND OF THE INVENTION

Vaccine development and usage over the years has significantly reduced the number of infections and diseases on a global basis. The need for vaccines persists, however, including for the treatment of emerging viral threats (e.g., SARS-COV-2) and other viral agents.

Vaccines are based on the use of an intact viral or bacterial agent, either inactivated or live attenuated, cloned expressed proteins using molecular biology techniques, or mRNA. These vaccines frequently require two or more injections intramuscularly to develop a significant immune response. Additional boosters may be necessary to sustain immunity.

There remains a need for novel vaccine strategies, including novel adjuvanted protein vaccine strategies, particularly for emerging and recalcitrant bacterial, viral, and parasitic diseases. There also remains a need for vaccines that can be delivered subcutaneously.

SUMMARY OF THE INVENTION

Disclosed herein are features of adjuvanted protein vaccines that can be administered subcutaneously or intramuscularly, and methods for preparing and using the same.

In a first aspect, an adjuvanted protein vaccine is disclosed, the vaccine comprising: a non-phospholipid liposome and one or more proteins, wherein the protein is encapsulated within the non-phospholipid liposome, and wherein the protein is selected from:

(i) a modified full-length spike protein that generates IgG antibody responses for 120 days after two injections of the adjuvanted protein vaccine, by subcutaneous or intramuscular routes;

(ii) a modified spike protein sequence of a coronavirus;

(iii) a protein sequence from a coronavirus; and (iv) a protein from an infectious agent that generates IgG antibody responses to proteins after one or two subcutaneous or intramuscular injections.

In a second aspect, a modified spike protein sequence containing a modified full-length SARS-COV-2 spike protein sequence is disclosed.

In a third aspect, a method for generating an immune response in a subject comprising administering an adjuvanted protein vaccine to the subject.

In a fourth aspect, a method for preventing an infection in a subject comprising administering an adjuvanted protein vaccine to the subject.

BRIEF DESCRIPTION OF THE FIGURES

Figure 12:
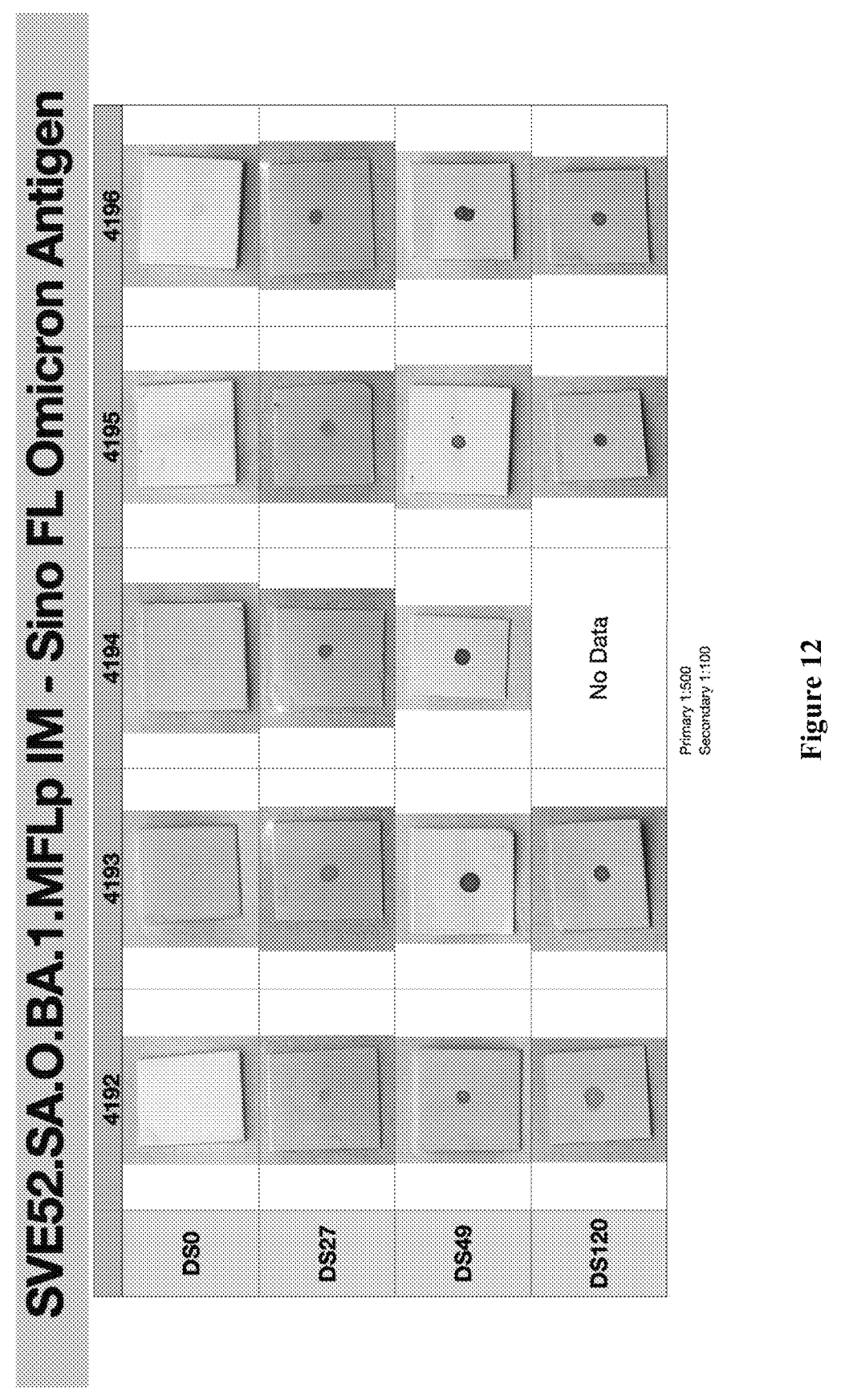

FIG. 12 depicts blot images for IgG antibodies directed against the Sino Omicron Antigen full-length Spike protein of the SARS-COV-2. The animals were immunized intramuscularly with a SVE52 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. Antibody responses by blot to the Sino Omicron Spike Antigen were noted in all animals tested at days 27, 49, and 120.

Figure 14:
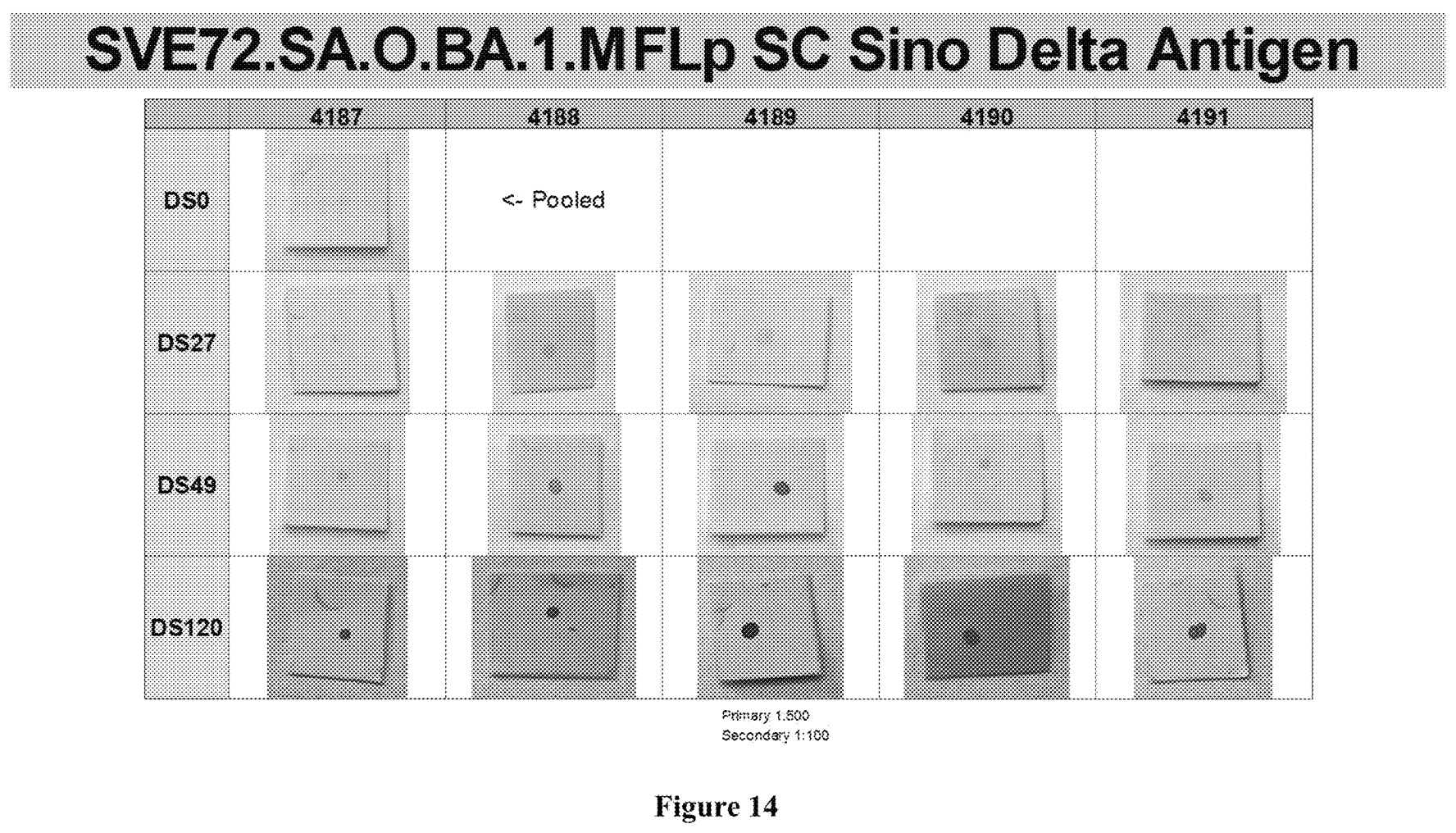

FIG. 14 depicts blot images for IgG antibodies directed against the Sino Delta Antigen full-length Spike protein of the SARS-COV-2. The animals were subcutaneously immunized with a SVE72 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. Antibody responses by blot to the Sino Delta Spike Antigen were noted in five of five animals at day 120.

Figure 17:
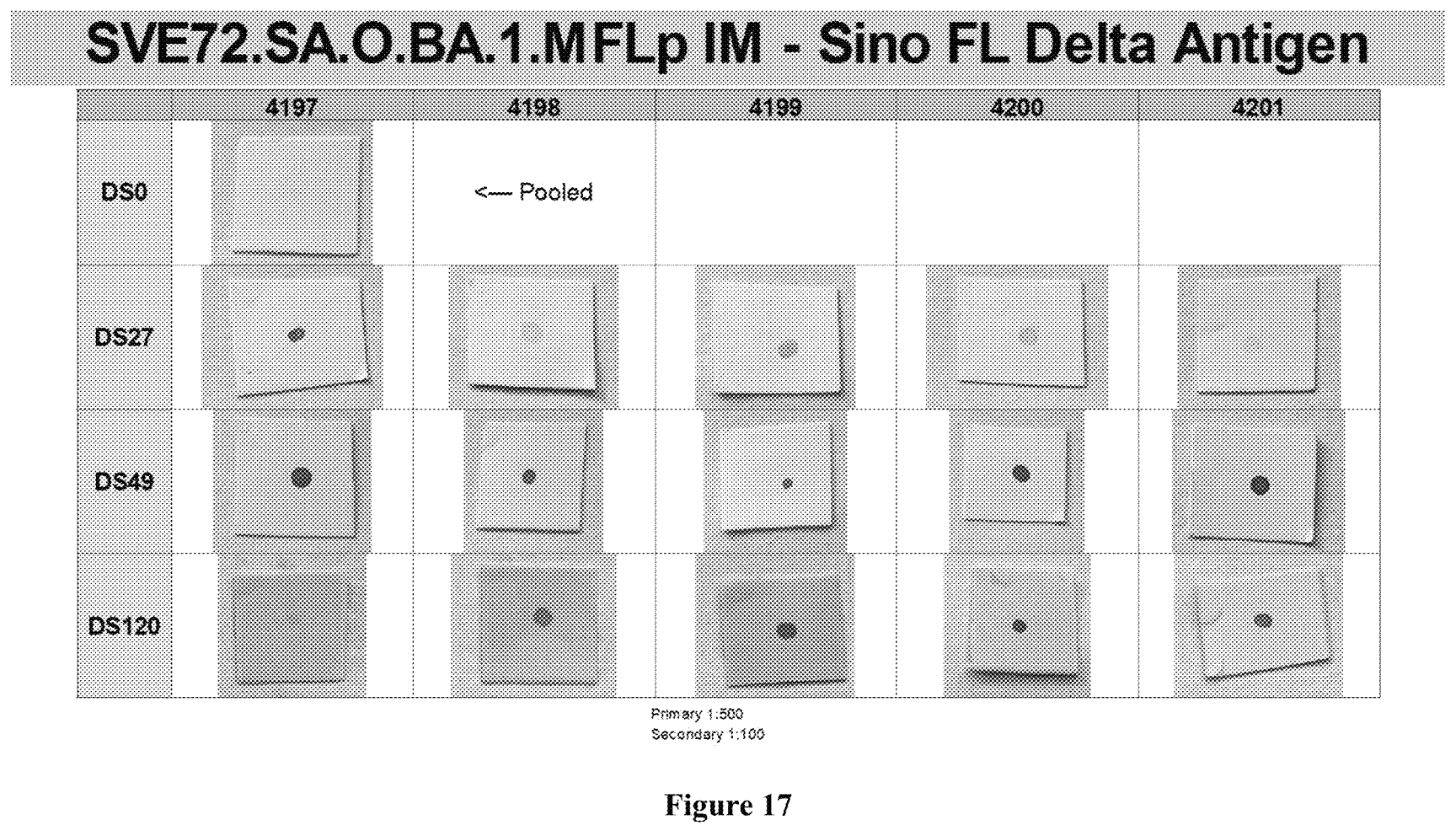

FIG. 17 depicts blot images for IgG antibodies directed against the Sino Delta Antigen full-length Spike protein of the SARS-COV-2. The animals were immunized intramuscularly with a SVE72 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. Antibody responses by blot to the Sino Delta Spike Antigen were noted in two of five animals at day 27, five of five animals at day 49, and four of five at day 120.

Figure 20:
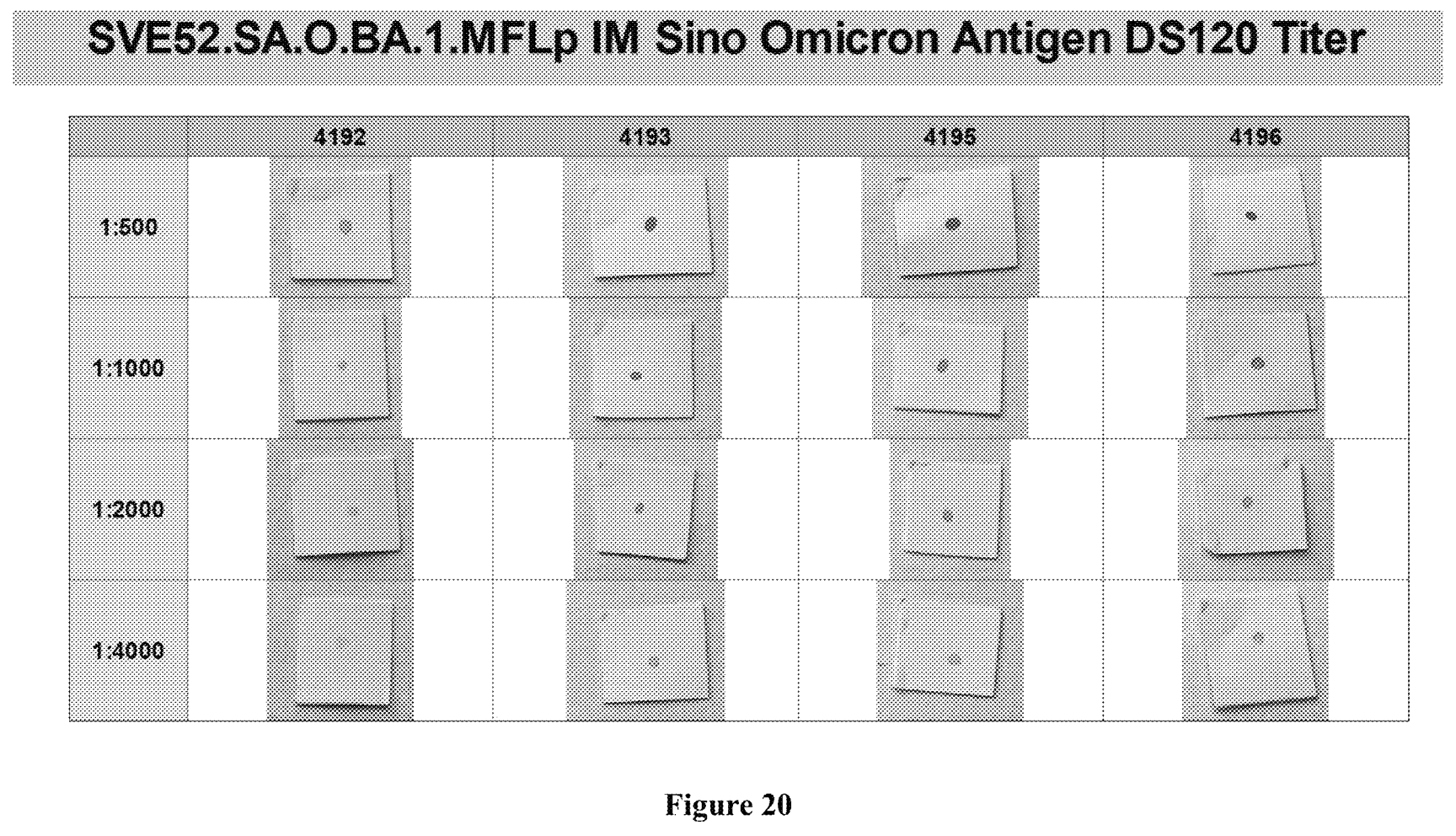

FIG. 20 depicts blot images for IgG antibodies directed against the Sino Omicron Antigen full-length Spike protein of the SARS-COV-2. The animals were immunized intramuscularly with a SVE52 non-phospholipid liposome containing vitamin E and a modified full-length sequence of the Omicron BA.1 variant of SARS-COV-2 (SEQ. ID No. 3). The day 120 bleed was tested in a serum dilution assay out to 1:4000. Four out of four animals were positive out to a dilution of sera at 1:2000.

Figure 21:
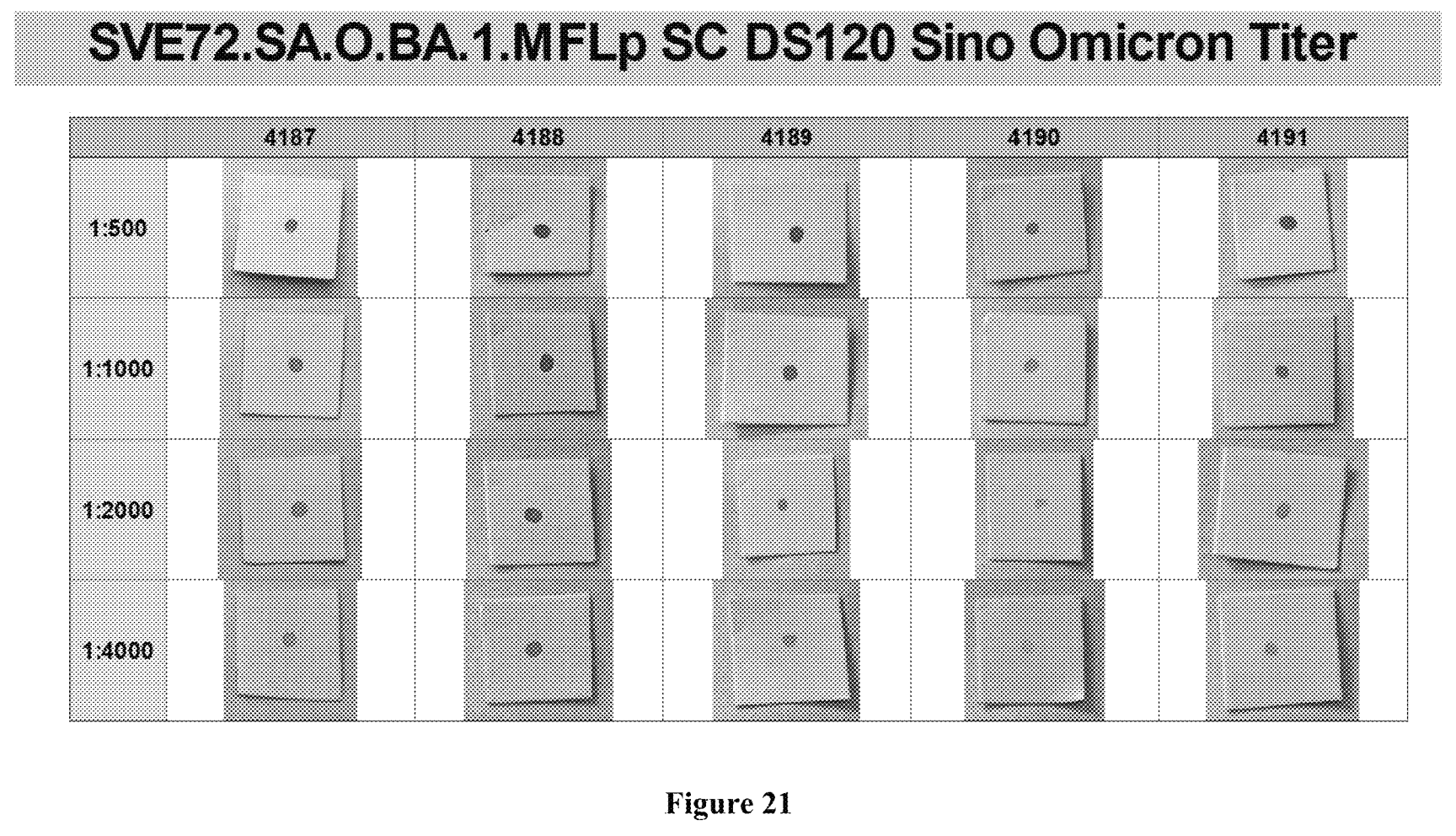

FIG. 21 depicts blot images for IgG antibodies directed against the Sino Omicron Antigen full-length Spike protein of the SARS-COV-2. The animals were immunized subcutaneously with a SVE72 non-phospholipid liposome containing vitamin E and a modified full-length sequence of the Omicron BA.1 variant of SARS-COV-2 (SEQ ID No. 3). The day 120 bleed was tested in a serum dilution assay out to 1:4000. Four out of five animals were positive out to a dilution of sera at 1:4000.

DETAILED DESCRIPTION OF THE INVENTION

Definitions

Figure 1:
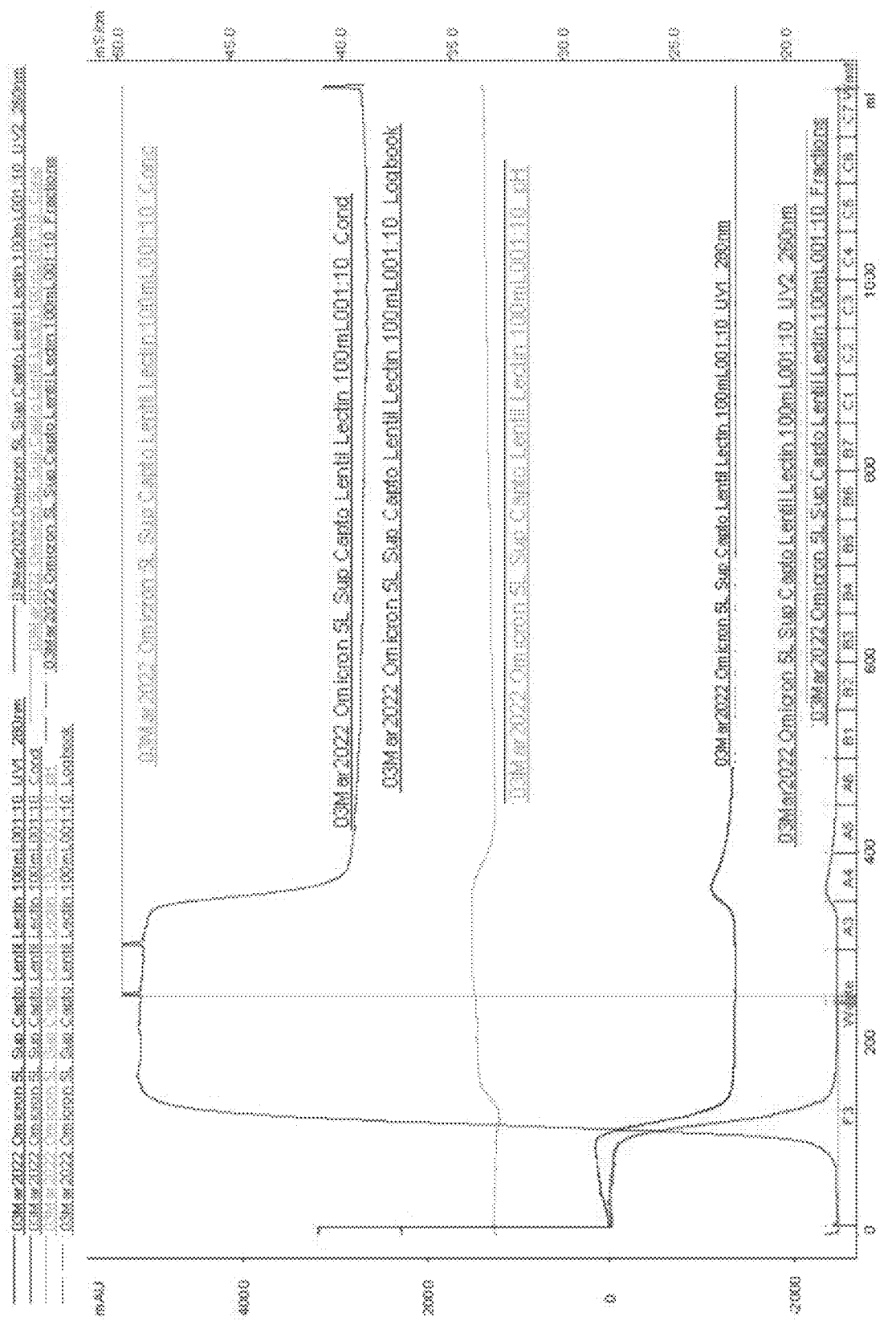
FIGS. 1, 2 and 3 depict chromatography graphs of the resulting solutions from purification of clarified cell culture supernatant containing the modified full length spike protein of Omicron BA.1 (SEQ. ID. No. 3) with affinity chromatography resin. The chromatography graphs were obtained at 0 days (FIG. 1), 11 days (FIG. 2) and 25 days (FIG. 3).

The term "about" as used herein refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

The term "adjuvant" as used herein refers to a substance whose admixture with an administered immunogenic determinant/antigen construct increases or otherwise modifies the immune response to said determinant. Immunological adjuvants function by attracting macrophages to the antigen and then to presenting said antigens to the regional lymph nodes and initiating an effective antigenic response. Conventional adjuvants can serve as vehicles for the antigen, and as nonspecific immunological stimulants. In one embodiment, the liposome (e.g., the paucilamellar liposome) serves as an adjuvant for the glycoprotein vaccine disclosed herein and in certain embodiments, incorporates Vitamin E.

The term "administering" as used herein means either directly administering a compound or composition of the present invention. Any route of administration, such as topical, subcutaneous, peritoneal, intravenous, intraarterial, inhalation, vaginal, rectal, nasal, buccal, introduction into the cerebrospinal fluid, or instillation into body compartments can be used. The terms and phrases "administering" and "administration of," when used in connection with a compound or pharmaceutical composition (and grammatical equivalents) refer both to direct administration, which may be administration to a patient by a medical professional or by self-administration by the patient, and/or to indirect administration, which may be the act of prescribing a drug.

The term "affinity" as used herein refers to the equilibrium constant for the reversible binding of two agents and is expressed as a dissociation constant (KD).

The term "amino acid" or "amino acids" as used herein is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers). Abbreviations for amino acids are well understood in the art.

The term "amphiphilic" as used herein means exhibiting characteristics of hydrophilicity and lipophilicity. Common amphiphilic substances are soaps, detergents and lipoproteins. Other examples of amphiphilic compounds are: saponins, phospholipids, glycolipids, polysorbates.

The term "antigen" as used herein refers to a molecule with one or more epitopes that stimulate a host's immune system to make a secretory, humoral and/or cellular antigen-specific response, or to a DNA molecule that is capable of producing such an antigen in a vertebrate. The term is also used interchangeably with "immunogen." For example, a specific antigen can be complete protein, portions of a protein, peptides, fusion proteins, glycosylated proteins and combinations thereof.

The term "binding" as used herein refers to direct association between two molecules, due to, for example, covalent, electrostatic, hydrophobic, and ionic and/or hydrogen-bond interactions, including interactions such as salt bridges and water bridges. "Specific binding" refers to binding with an affinity of at least about 10-7 M or greater.

The term "boost" as used herein refers to the administration of an additional dose of an immunizing agent, such as a vaccine, administered at a time after the initial dose to sustain the immune response elicited by the previous dose of the same agent.

The term "carrier" as used herein includes any solvent(s), dispersion medium, coating(s), diluent(s), buffer(s), isotonic agent(s), solution(s), suspension(s), colloid(s), inert (s), or such like, or a combination thereof that is pharmaceutically acceptable for administration to the relevant animal or acceptable for a therapeutic or diagnostic purpose, as applicable.

The terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "conservative amino acid substitution" as used herein refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

The term "coronavirus" as used herein refers to positive strand RNA viruses with the largest viral genome among the RNA viruses (27-33 kb). The virus particles are enveloped and carry extended spike proteins on the membrane surface, providing the typical crown-like structure. The coronaviruses share a conserved organization of their (positive strand) RNA genome. The 5' two-thirds of the genome contains the large 1a and 1b ORFs, encoding the proteins necessary for RNA replication (the nonstructural proteins), whereas the 3' one-third contains the genes coding for the structural proteins: haemagglutinin esterase protein (only for group IIa), spike protein, envelope protein, membrane protein and nucleocapsid protein. The accessory protein genes are interspersed between the structural protein genes and differ in number and position for the various coronavirus. Several coronavirus genera and subgenera are recognized. Among them, alpha- and betacoronaviruses infect mammals, gammacoronaviruses infect avian species, and delta-coronaviruses infect both mammalian and avian species. The coronavirus may be, for example, 229E, SARS, MERS, SARS-COV-1 (OC43), and SARS-COV-2. The coronavirus spike protein includes three segments: a large ectodomain, a single-pass transmembrane anchor, and a short intracellular tail The ectodomain consists of a receptor-binding subunit S1 and a membrane-fusion subunit S2. The S1 and S2 domains may be separated by a cleavage site that is recognized by furin-like proteases during S protein biogenesis in the infected cell. The spike protein binds to a receptor on the host cell surface through the S1 subunit and then fuses viral and host membranes through its S2 subunit. The spike protein exists in two structurally distinct conformations, pre-fusion and post-fusion. The S1 subunit of the betacoronavirus spike proteins displays a multidomain architecture and is structurally organized in four distinct domains A-D of which domains A and B may serve as a Receptor Binding Domain (RBD).

The term "cross-reacts" as used herein refers to the reaction between an antigen and an antibody that was generated against a different but similar antigen.

The term "encapsulate" as used herein refers to the lipid vesicle forming an impediment to free diffusion into solution by an association with or around an agent of interest, e.g., a lipid vesicle may encapsulate an agent within a lipid layer or within an aqueous compartment inside or between lipid layers.

The term "identical" or percent "identity," in the context of two or more nucleic acids or polypeptide sequences, may refer to two or more sequences or subsequences that are the same or have a specified percentage of amino acid residues or nucleotides that are the same. In some cases, 2 or more sequences may be homologous (homologs) if they share at least 20%, 25%, 30%. 35%, 40%, 45%50%, 55%, 60%, 65%, 70%, 75%, 80%, 85%, 90%, 91%, 92%, 93%, 94%, 95%, 96%, 97%, 98%, 99%, or higher identity to a reference sequence when compared and aligned for maximum correspondence over a comparison window, or designated region as measured using one of the following sequence comparison algorithms or by manual alignment and visual inspection.

The term "incorporating" or "incorporated" as used herein with reference to a liposome means encapsulated/encapsulating into the cavity of the liposome, within the potential double layer of the liposome, or as part of the membrane layer of the liposome.

The term "immune response" as used herein refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (e.g., prevents infection or prevents the development of disease associated with infection). Methods of measuring immune responses are well known in the art and include, for example, by measuring proliferation and/or activity of lymphocytes (such as B or T cells), secretion of cytokines or chemokines, inflammation, antibody production and the like. "Enhancing an immune response" refers to co-administration of an adjuvant and at least one peptide, wherein the adjuvant increases the desired immune response to the at least one peptide compared to administration of the at least one peptide in the absence of the adjuvant.

The term "immunogenic composition" as used herein are those which result in specific antibody production or in cellular immunity when injected into a subject. In certain embodiments, the vaccine disclosed elicits a neutralizing antibody response.

The term "immunogenic variants" as used herein, refers to a variant that that is predicted to be immunogenic.

The term "liposome" as used herein refers to a vesicle made of concentric bilayers of lipids and more particularly, non-phospholipids or lipids which do not comprise phosphates groups. The liposome can be formed of the same lipid or different lipids. These lipids can have an anionic, cationic or zwitterionic hydrophilic head group. The size of a liposome may vary but is generally from about 10 to about 3000 nm. In certain embodiments, the liposome has an aqueous core, while in other embodiments, the liposome has an oil and water-filled core. The term "empty liposome" as used herein refers to a liposome not incorporating any peptide or other antigen within the liposome core.

The term "multilamellar" as used here refers to a vesicle containing more than one lipid bilayers.

The term "non-ionic surfactant" as used herein refers to a class of surfactants which have no charge groups in their hydrophilic heads. In solutions, nonionic surfactants form structures in which hydrophilic heads are opposite to aqueous solutions and hydrophilic tails are opposite to organic solutions. Representative, non-limiting non-ionic surfactants include alkyl esters, alkyl amides, alkyl ethers and esters of fatty acids.

The term "paucilamellar" as used herein refers to a vesicle having 2-10 lipid bilayers. In certain embodiments disclosed herein the vesicle that contains five or more polypeptides is paucilamellar.

The term "pharmaceutical composition" refers to a mixture of one or more chemicals, or pharmaceutically acceptable salts thereof, with a suitable carrier, for administration to a mammal as a medicine.

The term "phospholipid" as used herein refers to any of a group of lipids whose molecule has a hydrophilic "head" containing a phosphate group, and two hydrophobic "tails" derived from fatty acids, joined by a glycerol molecule. The phosphate group can be modified with simple organic molecules such as choline, ethanolamine or serine. In certain embodiments herein, the liposome does not contain phospholipids.

The term "prophylactic" as used herein with reference to an immunogenic composition (e.g., a vaccine) that is administered to a subject who does not exhibit signs of a disease.

The term "protein" as used herein refers to a sequence of amino acid residues between 600 and 1,300 amino acids in length.

The term "recombinant" as used herein refers to intended to refer to proteins that are designed, engineered, prepared, expressed, created, or isolated by recombinant means, such as proteins expressed using a recombinant expression vector transfected into a host cell, proteins isolated from a recombinant, combinatorial proteins library, or proteins prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. In some embodiments, one or more such selected sequence elements results from the combination of multiple (e.g., two or more) known sequence elements that are not naturally present in the same protein.

The term "spike protein", as used herein, refers to a type I transmembrane glycoprotein that is characteristic of coronaviruses. Most spike proteins contain a leader, an ectodo-main, a transmembrane domain and an intracellular tail.

The term "subject in need thereof" as used herein refers to a living organism suffering from or prone to a disease or condition that can be treated by using the methods provided herein. The term does not necessarily indicate that the subject has been diagnosed with a particular disease or disorder, but typically refers to an individual under medical supervision. Non-limiting examples include humans, other mammals, bovines, rats, mice, dogs, monkeys, goat, sheep, cows, deer, and other non-mammalian animals. In embodi-ments, a patient is human.

The term "therapeutic activity" or "activity" may refer to an activity whose effect is consistent with a desirable thera-peutic outcome in humans, or to desired effects in non-human mammals or in other species or organisms. Thera-peutic activity may be measured in vivo or in vitro. For example, a desirable effect may be assayed in cell culture.

The terms "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physi-ological symptoms associated with the underlying disorder such that an improvement is observed in the patient, not-withstanding that the patient may still be afflicted with the underlying disorder. For prophylactic benefit, the composi-tions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the dis-ease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective com-position after their initial appearance; preventing re-occur-ring of the disease and/or relieving the disease, that is, causing the regression of clinical symptoms by administra-tion of a protective composition after their initial appear-ance.

The term "vaccine" as used herein, refers to any type of biological preparation contributing to or soliciting active immune responses against a particular disease or pathogen. Such biological preparation can include, but is not limited to, an antigen derived from a disease-causing agent or a portion of an antigen derived from a disease-causing agent.

The term "vaccination" or "vaccinate" refers to the administration of a composition intended to generate an immune response, for example to a disease-causing agent. Vaccination can be administered before, during, and/or after exposure to a disease-causing agent, and/or to the develop-ment of one or more symptoms, and in some embodiments, before, during, and/or shortly after exposure to the agent. In some embodiments, vaccination includes multiple adminis-trations, appropriately spaced in time, of a vaccinating composition.

The term "vaccine efficacy" or "VE" as used herein measure the proportionate reduction in cases among vacci-nated persons. It is measured by calculating the risk of disease among vaccinated and unvaccinated persons and determining the percentage reduction in risk of disease among vaccinated persons relative to unvaccinated persons. The greater the percentage reduction of illness in the vac-cinated group, the greater the vaccine efficacy.

The term "variant" as used refers to a polynucleotide sequence related to a wild type gene. This definition may also include, for example, "allelic," "splice," "species," or "polymorphic" variants. A splice variant may have signifi-cant identity to a reference molecule, but will generally have a greater or lesser number of polynucleotides due to alter-nate splicing of exons during mRNA processing. The cor-responding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or func-tion may or may not be altered. Any given natural or recombinant gene may have none, one, or many allelic forms. Common mutational changes that give rise to vari-ants are generally ascribed to natural deletions, additions, or substitutions of nucleotides. Each of these types of changes may occur alone, or in combination with the others, one or more times in a given sequence. A "variant" of a protein may have at least 70%, 75%, 80%, 85%, 90%, 95%, 98% or 99% amino acid identity over a stretch of 10, 20, 30, 50, 75 or 100 amino acids of such protein. Variants of the proteins as defined herein, which may be encoded by a nucleic acid molecule, may also comprise those sequences, wherein nucleotides of the encoding nucleic acid sequence are exchanged according to the degeneration of the genetic code, without leading to an alteration of the respective amino acid sequence of the protein, i.e., the amino acid sequence or at least part thereof may not differ from the original sequence in one or more mutation(s) within the above meaning.

The term "vesicle" as used herein refers to a structure comprising liquid or cytoplasm enclosed by a lipid bilayer. The interior of the vesicle is typically an aqueous environ-ment but can also be an oily environment, and it may comprise an agent such as but not limited to a prophylactic, therapeutic or diagnostic agent.

Disclosed herein are immunogenic compositions, such as adjuvanted vaccine, which comprise a lipid vesicle, such as a non-phospholipid liposome, and one or more proteins, wherein the protein is encapsulated within the lipid vesicle. Various proteins can be used in the compositions, including but not limited to:

(i) a modified full-length spike protein that generates IgG antibody responses for 120 days after two injections of the adjuvanted protein vaccine, by subcutaneous or intramuscular routes;

(ii) a modified spike protein sequence of a coronavirus;

(iii) a protein sequence from a coronavirus; and (iv) a protein from an infectious agent that generates IgG antibody responses to proteins after one or two subcu-taneous or intramuscular injections.

Also disclosed herein are non-phospholipid liposomes, which can be used in the immunogenic compositions. In certain embodiments, the non-phospholipid liposome com-prises Vitamin E.

Modified spike protein sequences containing a modified full-length SARS-COV-2 spike protein sequence are also disclosed.

Methods of use of the immunogenic compositions, liposomes and sequences are also disclosed herein.

Administration of standard vaccines intramuscularly results in significant pain and swelling at the injection site. Other more serious reactions may occur. Advantageously, the immunogenic compositions or vaccines disclosed herein can be administered subcutaneously. In certain embodiments, the vaccines require a single vaccination with one boost for efficacy. In certain embodiments, the vaccines can be stored at refrigerated temperatures.

Compositions

The present disclosure provides immunogenic (or pharmaceutical) compositions, such as vaccines. In one embodiment, the composition is an adjuvanted protein vaccine comprising one or more proteins and a lipid vesicle, such as a liposome. In certain embodiments, one or more proteins is encapsulated within a liposome. These compositions are suitable for use, for example, in generating an immune response as described further herein. In certain embodiments, the vaccine facilitates generation of IgG antibodies to spike proteins from multiple SARS-COV-2 variants.

In one embodiment, the composition is an adjuvanted SARS-COV-2 spike protein vaccine.

Proteins

The compositions (e.g., vaccines) disclosed herein include one or more proteins. In certain embodiments, the compositions could contain a combination of proteins. In certain embodiments, the composition or vaccine comprises at least one, at least two, at least three, or at least four, or at least five or more proteins.

In certain embodiments, the immunogenic composition cross-reacts with full-length SARS-COV-2 spike proteins.

In one embodiment, the one or more proteins are selected from:

(i) a modified full-length spike protein that generates IgG antibody responses for 120 days after two injections of the adjuvanted protein vaccine, by subcutaneous or intramuscular routes;

(ii) a modified spike protein sequence of a coronavirus;

(iii) a protein sequence from a coronavirus; and (iv) a protein from an infectious agent that generates IgG antibody responses to proteins after one or two subcutaneous or intramuscular injections.

In one embodiment, the protein is a modified full-length spike protein, for example a modified full-length spike protein that generates IgG antibody responses for 120 days after two injections of the adjuvanted protein vaccine, by subcutaneous or intramuscular routes.

In one embodiment, the protein is a modified spike protein sequence of a coronavirus. In one embodiment, the modified spike protein sequence of a coronavirus is a modified full-length spike protein from the SARS-COV-2 Omicron BA.1 variant. In one embodiment, the modified full-length spike protein from the SARS-COV-2 Omicron BA.1 variant is SEQ. ID. No. 3.

In one embodiment, the protein is a protein sequence from a coronavirus.

In one embodiment, the protein is a protein from an infectious agent, for example an infectious agent that generates IgG antibody responses to proteins after one or two subcutaneous or intramuscular injections.

In one embodiment, the viral protein is derived from a DNA virus selected from the group consisting of adenovirus, papillomavirus, parvovirus, herpes simplex virus, varicella-zoster virus, cytomegalovirus, Epstein-Barr virus, smallpox virus, vaccinia virus, and hepatitis B virus.

In another embodiment the viral protein is derived from an RNA virus selected from the group consisting of tavirus, norovirus, enterovirus, hepatovirus, rubella virus, influenzaviruses (A, B, and C), measles virus, mumps virus, hepatitis C virus, yellow fever virus, hantavirus, Zika virus, California encephalitis virus, rabies virus, Ebola virus, and HIV.

In one embodiment, the viral protein is from a coronavirus. The coronavirus can be any coronavirus currently known, or later discovered. In certain embodiments, the coronavirus is zoogenic.

In a particular embodiment, the viral protein is from SARS-COV-2 or a variant thereof. SARS-COV-2 can cause severe respiratory illness and significant mortality among those over 65 years old or with chronic conditions. Infection of target cells by SARS-COV-2 is mediated through the interaction of the viral Spike (S) protein (1273 amino acids or fewer) and its cellular receptor, angiotensin-converting enzyme 2 (ACE2). The SARS-COV-2 receptor-binding domain in SEQ. ID No. 2 (amino acids 319-541) includes a region along its periphery that contacts ACE2 and is designated the receptor-binding motif (in SEQ. ID. No. 2 amino acids 438-508).

In one embodiment, the viral protein is derived from the spike (S) protein of the coronavirus. Other relevant proteins like envelope (E), membrane (M), nucleocapsid (N) protein of the coronavirus or a combination thereof could occur.

In certain embodiments, the vaccine contains at least one protein from SEQ. ID NO: 1, which is the SARS-COV-2 Omicron BA.1 Spike Protein sequence.

In certain embodiments, the protein is a SARS-COV-2 spike protein, such as the spike protein of the Omicron BA.1 variant or a modified version thereof. In certain embodiments, the protein is a modified full length Omicron BA.1 spike protein with His-tag containing 1118 amino acids: 1107 amino acids in the modified Omicron BA.1 and an 11 amino acid His-tag (SEQ. ID No. 3).

The Omicron BA.1 construct contains 6 amino acids deletions in the spike protein, a 3 amino acid insertions in the spike protein, and 35 single amino acid substitutions in the spike protein. The terminal 163 amino acids from parent spike protein of 1270 amino acids was removed. In deleting these 163 amino acids we have deleted we have deleted three sequences, each of which has homology to at least one human protein.

One sequence in the spike protein VMTIMLCCMTSCCSCLKGC (SEQ. ID No. 4) at amino acids 1228-1247 has sequence homology to CCMSSCC (SEQ. ID No. 5) which is found in keratin associated protein 4-7 (KRTAP4-7) in human skin. The same sequence in the spike protein VMTIMLCCMTSCCSCLKGC (SEQ. ID No. 4) at amino acids 1228-1247 has sequence homology to CKTSCCSC (SEQ. ID No. 6) in Metallothionein 1 E (MTIE) found in human liver and many other tissues.

A second sequence in the spike protein LNEVAKNLNESLIDLQELGK (SEQ. ID No. 7) at amino acids 1186-1205 has sequence homology to KNMEEGLITLQEL (SEQ. ID No. 8) which is found in human Coiled-containing domain-containing protein 175 isoform X8 which is found in human brain, pituitary gland, and testis.

A third sequence in the spike protein LNEVAKNLNESL-IDLQELGK (SEQ. ID No. 7) at amino acids 1186-1205 has sequence homology to KNLNQSLLDLHALG (SEQ. ID No. 9) which is found in human hCG23535 which is apart of the human genome.

A fourth sequence in the spike protein KEELDKYFKNHTSPDVDLGD (SEQ. ID No. 10) at amino acids 1149-1168 has sequence homology to EILDKYFKN (SEQ. ID No. 11) which is found in Follistatin-related protein 1 isoform X1 in human placenta.

Additionally, the spike protein sequence in the furin cleavage site sequence HRRAR (SEQ. ID No. 12) was changed to KKKAK (SEQ. ID No. 13) to make the construct protease resistant. The 11 amino acid His-tag, QGPSPHHHHHH (SEQ. ID No. 14), was added for purification purposes.

Final construct is 1107 Amino Acids of the modified Omicron BA.1 spike protein with an additional 11 amino acid His-tag (SEQ. ID No. 3), which is shown below with the His-tag is depicted in black bolding at the C terminus of the construct. The furin cleavage site changes are also depicted in bold:

```
MFVFLVLLPL VSSQCVNLTT RTQLPPAYTN SFTRGVYYPD

KVFRSSVLHS TQDLFLPFFS NVTWFHVISG TNGTKRFDNP

VLPFNDGVYF ASIEKSNIIR GWIFGTTLDS KTQSLLIVNN

ATNVVIKVCE FQFCNDPFLD HKNNKSWMES EFRVYSSANN

CTFEYVSQPF LMDLEGKQGN FKNLREFVFK NIDGYFKIYS

KHTPIIVEPE RDLPQGFSAL EPLVDLPIGI NITRFQTLLA

LHRSYLTPGD SSSGWTAGAA AYYVGYLQPM TYILKYNENG

TITDAVDCAL DPLSETKCTL KSFTVEKGIY QTSNFRVQPT

ESIVRFPNIT NLCPFDEVEN ATRFASVYAW NRKRISNCVA

DYSVLYNLAP FFTFKCYGVS PTKLNDLCFT NVYADSFVIR

GDEVRQIAPG QTGNIADYNY KLPDDFTGCV IAWNSNKLDS

KVSGNYNYLY RLFRKSNLKP FERDISTEIY QAGNKPCNGV

AGENCYFPLK SYSFRPTYGV GHQPYRVVVL SFELLHAPAT

VCGPKKSTNL VKNKCVNFNF NGLKGTGVLT ESNKKFLPFQ

QFGRDIADTT DAVRDPQTLE ILDITPCSFG GVSVITPGTN

TSNQVAVLYQ GVNCTEVPVA IHADQLTPTW RVYSTGSNVF

QTRAGCLIGA EYVNNSYECD IPIGAGICAS YQTQTKSKKK

AKSVASQSII AYTMSLGAEN SVAYSNNSIA IPNNFTISVT

TEILPVSMTK TSVDCTMYIC GDSTECINLL LQYGSFCTQL

KRALTGIAVE QDKNTQEVFA QVKQIYKTPP IKYFGGFNFS

QILPDPSKPS KRSFIEDLLF NKVTLADAGF IKQYGDCLGD

IAARDLICAQ KFKGLTVLPP LLTDEMIAQY TSALLAGTIT

SGWTFGAGAA LQIPFAMQMA YRFNGIGVTQ NVLYENQKLI

ANQFNSAIGK IQDSLSSTAS ALGKLQDVVN HNAQALNTLV

KQLSSKFGAI SSVLNDIFSR LDKVEAEVQI DRLITGRLQS

LQTYVTQQLI RAAEIRASAN LAATKMSECV LGQSKRVDFC

GKGYHLMSFP QSAPHGVVFL HVTYVPAQEK NFTTAPAICH

DGKAHFPREG VFVSNGTHWF VTQRNFYQGP GSHHHHHH
```

Lipid Vesicle

The one or more proteins can be provided with, or encapsulated within, a lipid vesicle, such as a liposome.

Lipid vesicles are substantially spherical structures made of amphiphiles, e.g., surfactants or phospholipids. The lipids of these spherical vesicles are generally organized in the form of lipid bilayers, e.g., multiple onion-like shells of lipid bilayers which encompass an aqueous volume between the bilayers. Certain types of lipid vesicles have an unstructured central cavity which can be used to encapsulate and transport a variety of materials. The lipid vesicle may be charged or neutral.

The lipid vesicle may be any suitable lipid vesicle such as a liposome, e.g., a non-phospholipid (or a non-phospholipid-based) liposome. The liposome may comprise an adjuvanting oil. The lipid vesicle may be a unilamellar or multilamellar vesicle. Multilamellar vesicles are concentric circles constructed by at least 2 bilayer vesicles or a large vesicle embodying one or more small vesicles.

Liposome properties differ and may be selected on the basis of lipid composition, surface charge, size, and the method of preparation. Typically, liposomes can be divided into three categories based on their overall size and the nature of the lamellar structure. In one embodiment, the liposome is a small unilamellar vesicle (SUV) between about 20 and about 100 nm, a large unilamellar vesicle (LUV) greater than about 100 nm, a giant unilamellar vesicle (GULV) greater than about 100 nm, an oligolamellar vesicle (OLV) between about 100 and about 1000 nm or a multilamellar large vesicle (MLV) greater than about 500 nm.

In one embodiment, the lipid vesicle is a liposome formed from one or more non-phospholipid amphiphiles, such as one or more non-ionic surfactants and optionally, a membrane stabilizer such as cholesterol. Membrane stabilizers may be included to improve one or more properties of the liposome.

In certain embodiments, the lipid vesicle is a non-phospholipid-based liposome containing vitamin E. The lipid vesicle may be a unilamellar or multilamellar vesicle. Multilamellar vesicles are concentric circles constructed by at least 2 bilayer vesicles or a large vesicle embodying one or more small vesicles.

In one embodiment, the non-phospholipid liposome comprises: one or more polyoxyethylene fatty acid ethers, one or more membrane stabilizing agents, one or more negative charge producing agents, and Vitamin E. The non-phospholipid liposome may further comprise water, e.g., sterile water.

In one embodiment, the non-phospholipid liposome comprises one or more polyoxyethylene fatty acid ethers. In one embodiment, the one or more polyoxyethylene fatty acid ethers comprises polyoxyethylene 2-stearyl ether. In one embodiment, the one or more polyoxyethylene fatty acid ethers comprises polyoxyethylene 2-cetyl ether.

In one embodiment, the non-phospholipid liposome comprises one or more membrane stabilizing agents, for example a sterol. In one embodiment, the sterol is cholesterol. In one embodiments, the sterol is cholesterol derivative.

In one embodiment, the non-phospholipid liposome comprises one or more negative charge producing agents, for example oleic acid.

In one embodiment, the liposome suitable for use in a protein vaccine.

In one embodiment, the protein vaccine is suitable for subcutaneous or intramuscular administration.

In one embodiment, the lipid vesicle is a non-phospholipid-based liposome comprising, or consisting essentially of, polyoxyethelene 2-cetyl ether, cholesterol, oleic acid, vitamin E, and sterile water, and the non-phospholipid-based liposome contains the protein.

In one embodiment, the lipid vesicle is a non-phospholipid-based liposome comprising, or consisting essentially of, polyoxyethelene 2-stearyl ether, cholesterol, oleic acid, vitamin E, and sterile water, and the non-phospholipid-based liposome contains the protein.

In certain embodiments, the lipid vesicle or liposome comprises one or more polyoxyethylene fatty acid ether compound (e.g., polyoxyethelene 2-stearyl ether or polyoxyethelene 2-cetyl ether), one or more sterol compounds (e.g., a membrane stabilizer such as cholesterol), one or more negative-charge-producing agent (e.g., oleic acid), and Vitamin E. The lipid vesicle or liposome may further comprise any lipid soluble or water-soluble materials to be incorporated into the vesicles.

In certain embodiments, the lipid vesicle or liposome does not comprise phospholipids. In certain embodiments, the lipid vesicle or liposome does not comprise squalene.

In certain embodiments, the lipid vesicle or liposome comprises Vitamin E.

In certain embodiments, the lipid vesicle or liposome comprises sterile water.

In certain embodiments, the lipid vesicle or liposome contains or encompasses one or more proteins.

Liposome properties may differ and can be selected on the on the basis of lipid composition, surface charge, size, and the method of preparation.

In one embodiment, the lipid vesicle is a liposome selected from a small unilamellar vesicle (SUV) (10-100 nm), a large unilamellar vesicle (LUV) (100-3000 nm) and multilamellar vesicle (MLV). In certain embodiments, liposome is a vesicle comprising between 2 and about 10 layers. The 2 to 10 peripheral bilayers encapsulate an aqueous volume which is interspersed between the lipid bilayers and may also be encapsulated in the amorphous central cavity. Alternatively, the amorphous central cavity may be substantially filled with a water immiscible material, such as an oil or wax. The paucilamellar vesicles containing such amphiphiles provide a high carrying capacity for water-soluble and water immiscible substances. The high capacity for water immiscible substances represents a unique advantage over classical phospholipid multilamellar liposomes.

The lipid vesicle contains a central cavity, carrying either water soluble materials or a water-immiscible oily solution, which can be used to encapsulate the antigen or protein. The water-immiscible oily solution is made of materials which are both water immiscible and immiscible in the lipids used to form the bilayers. In certain embodiments, the water immiscible oily material found in the amorphous central cavity comprises Vitamin E.

In certain embodiments, oleic acid can insert in the membrane allowing negatively charged structures to be produced.

A. Pharmaceutical Composition

In certain embodiments, the immunogenic composition (e.g., vaccine) includes a pharmaceutically acceptable carrier. The pharmaceutically acceptable carrier may be formulated for administration to a human subject or animal.

In some embodiments, the pharmaceutically acceptable carrier includes diluents and adjuvants. Diluents include, for example, water or saline.

Compositions may be prepared as injectables, either as liquid solutions or suspensions. The composition may be prepared for nasal administration, e.g. as drops. Compositions may be presented in vials, or they may be presented in ready-filled syringes. The syringes may be supplied with or without needles. A syringe will include a single dose of the composition, whereas a vial may include a single dose or multiple doses.

The composition may be packaged in unit dose form or in multiple dose form.

B. Methods of Use

The compositions and vaccines described herein are useful, for example, for generating an immune response. Generally, the method includes contacting the cell with an effective amount of the compositions or vaccines described herein.

In some embodiments, methods of inducing an immune response are used for vaccination. The methods involve administering a prophylactically effective amount of the immunogenic composition as described herein to prevent an infection by, or an amount sufficient to reduce the biological activity of, an infectious agent such as a virus (e.g., a coronavirus).

In one embodiment, a method for generating an immune response in a subject comprises administering an adjuvanted protein vaccine to the subject.

In one embodiment, a method for preventing an infection in a subject comprises administering an adjuvanted protein vaccine to the subject.

In one embodiment, the method comprises administering an adjuvanted protein vaccine is subcutaneously or intramuscularly. In one embodiment, the method generates an IgG immune response. In one embodiment, the method increases the immune response to SARS-COV-2 spike protein. In one embodiment, the method comprises administering the adjuvanted protein vaccine in one or more doses.

In certain embodiments, the vaccine is a prophylactic vaccine, i.e., confers immunity to a subject who is not infected. According to this embodiment, the method comprising administering the vaccine to a subject in need thereof. In certain embodiments, administration is subcutaneously.

For example, and without limitation, the one or more subsequent exposures occurring administration may result in reduced viral titers, reduced amount and/or severity of symptoms, shortened duration of symptoms, and/or reduced need for treatment medications and/or clinician oversight, as compared to a control.

In certain embodiments, the immunogenic composition (e.g., vaccine) is administered to a subject as a single dose followed by a second dose later. In one embodiment the immunogenic composition (e.g., vaccine) and/or booster administrations may be repeated and such administrations may be separated by at least 28 days after the initial dose.

In one embodiment, the vaccine disclosed herein is administered as a booster to one or more vaccines known in the art. In a particular embodiment, the vaccine disclosed herein is administered as a booster to an mRNA vaccine or an adenoviral vaccine. In a particular embodiment, the vaccine disclosed herein is a booster to a SARS-COV-2 vaccine selected from the Pfizer-BioNTech COVID-19 vaccine, the Moderna COVID-19 vaccine, the Janssen COVID-19 vaccine, or the Novavax COVID-19 vaccine.

Administration may be by any suitable mode known in the art. In a particular embodiment, administration is subcutaneous.

The useful dosage administered may vary. In one embodiment, the suitable dose is about 2 μg of antigen.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least about 3 weeks apart, more particularly about 4 weeks apart.

The subject may be an animal, preferably a vertebrate, more preferably a mammal. Exemplary subject includes, e.g., a human, a cow, a pig, a chicken, a cat or a dog, as the infectious agents covered herein may be problematic across a wide range of species. Where the vaccine is for prophylactic use, the human is preferably a teenager, or an adult.

Methods of Preparation

The immunogenic compositions (e.g., vaccines) disclosed herein may be prepared by any suitable method.

The protein of the immunogenic composition disclosed herein can be made in any suitable way. Proteins are chemically synthesized.

Once a lipophilic phase is made, it is blended with an aqueous phase (e.g., water, saline, or any other aqueous solution which will be used to hydrate the lipids), which contain protein antigens, under shear mixing conditions to form the adjuvanted protein vaccine.

In one embodiment, the lipid vesicle is prepared utilizing high sheer technology.

In one embodiment, the lipid vesicle (e.g., non-phospho-lipid-based liposome) is loaded by direct entrapment.

The final concentration of peptide in the adjuvanted vaccine may vary. In one embodiment, the final concentration is 2 µg of protein in each vaccine dose.

In certain embodiments, the vaccine is manufactured using cell culture technique, such as that which is used commercially to produce a baculovirus-expressed SARS-COV-2 spike protein based on the original Wuhan Hu-1 sequence of SARS-COV-2 from December 2019.

The following Examples are intended to be non-limiting.

EXAMPLES

Example 1: Preparation of an Exemplary Protein

A. Expression of Gene of Interest (GOI), modified full length spike protein of Omicron BA.1 (SEQ. ID No. 3) in Baculovirus Expression Vector System 1. Synthesis and Cloning of GOI into Transfer Vector.

The GOI sequence (SEQ ID NO. 3) was based on the modified full length spike protein of Omicron BA.1 (SEQ ID NO. 2) provided by D4 Labs LLC. The gene was designed by optimization of nucleotide codon bias for high-level expression in insect cells. The gene was biochemically synthesized de novo and cloned into pFastBac1-baculovirus transfer vector. The GOI sequence and adjacent vector sequences were confirmed by DNA sequencing.

2. Cloning or GOI from Transfer Vector into Recombinant Baculovirus.

Bac-to-Bac™ system (Thermo Fisher™ Invitrogen™) was used for Cloning or GOI from transfer vector into recombinant baculovirus. Recombinant bacmids were produced by site-specific homologous recombination following transformation of bacmid transfer pFastBac1-GOI plasmids containing GOI into E. coli DH10Bac competent cells, which contained the AcMNPV baculovirus genome (Invitrogen™). The recombinant bacmid DNA was transfected into the Sf9 insect cells seeded in 6-well plates at 0.5×106 cells/ml using Fugene 6 reagent (Invitrogen™ protocol). At 72 h post-transfection, cells were harvested for recovery in the culture medium of recombinant baculoviruses containing GOI.

3. Cell Culture and Baculovirus Infections.

Spodoptera frugiperda Sf9 insect cells (ATCC CRL-1711) were maintained as suspension cultures in Sf900-II insect serum free medium (Thermo Fisher™) at 28° C. Plaque isolates expressing GOI were amplified by infecting Sf9 cells seeded in shaker flasks at 2×106 cells/ml at a multiplicity of infection (MOI)=0.05. At 72 h post-infection, culture supernatants containing the recombinant baculoviruses were harvested, clarified by centrifugation, and stored at 4° C. Titers of recombinant baculovirus stocks were determined by agarose plaque assay in Sf9 cells.

4. GOI Protein Expression

For protein expression, Sf9 cells were infected in 200-1000 ml volume for 72 h at a cell density of 2×106 cells/ml with recombinant baculoviruses at a MOI=3. Expression of GOI protein was determined by SDS-PAGE using 4-12% gradient polyacrylamide gels (Invitrogen™) and Coomassie staining and by Western blotting using antigen-specific sera.

Figure 2:
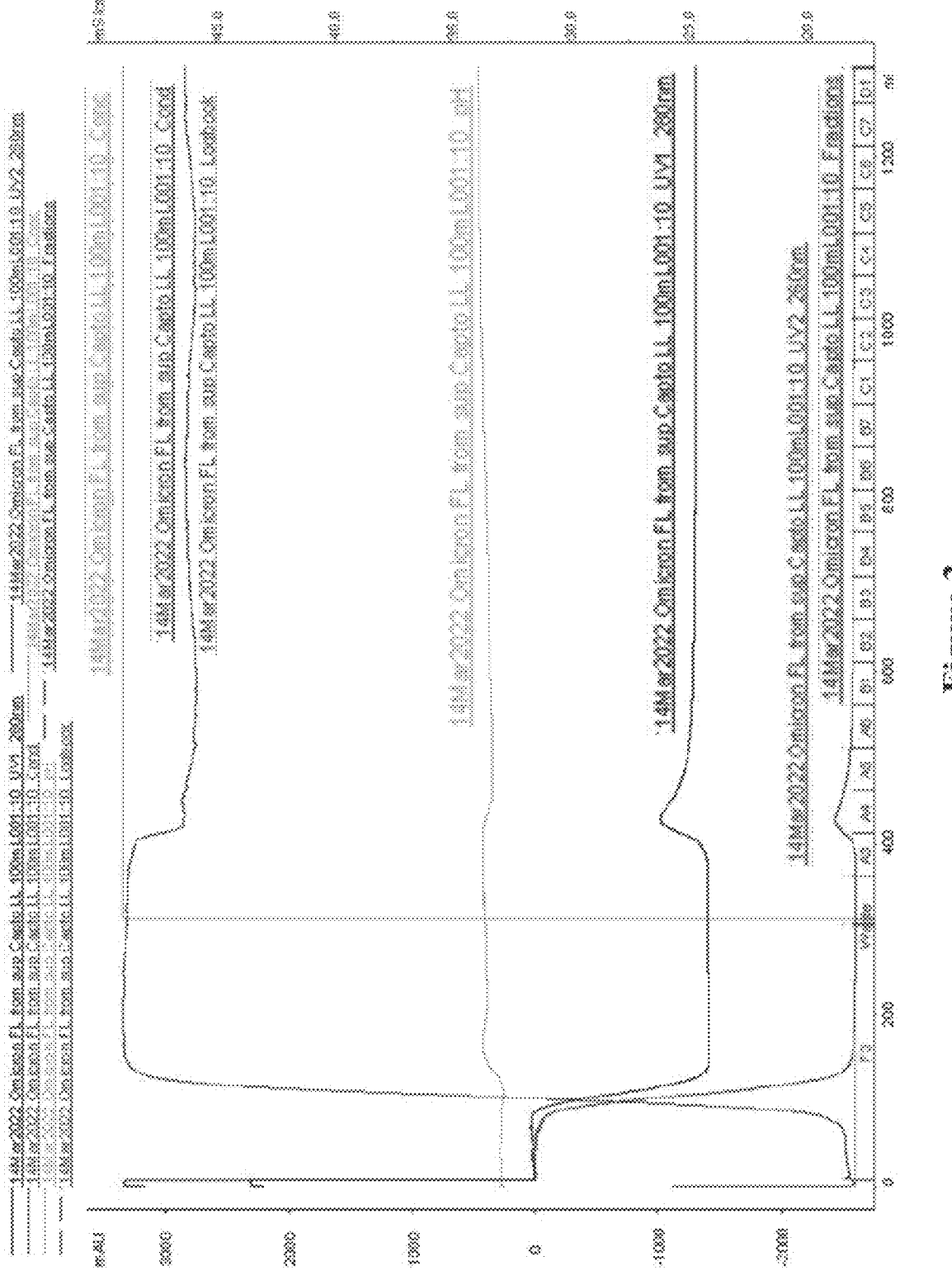
Figure 3:
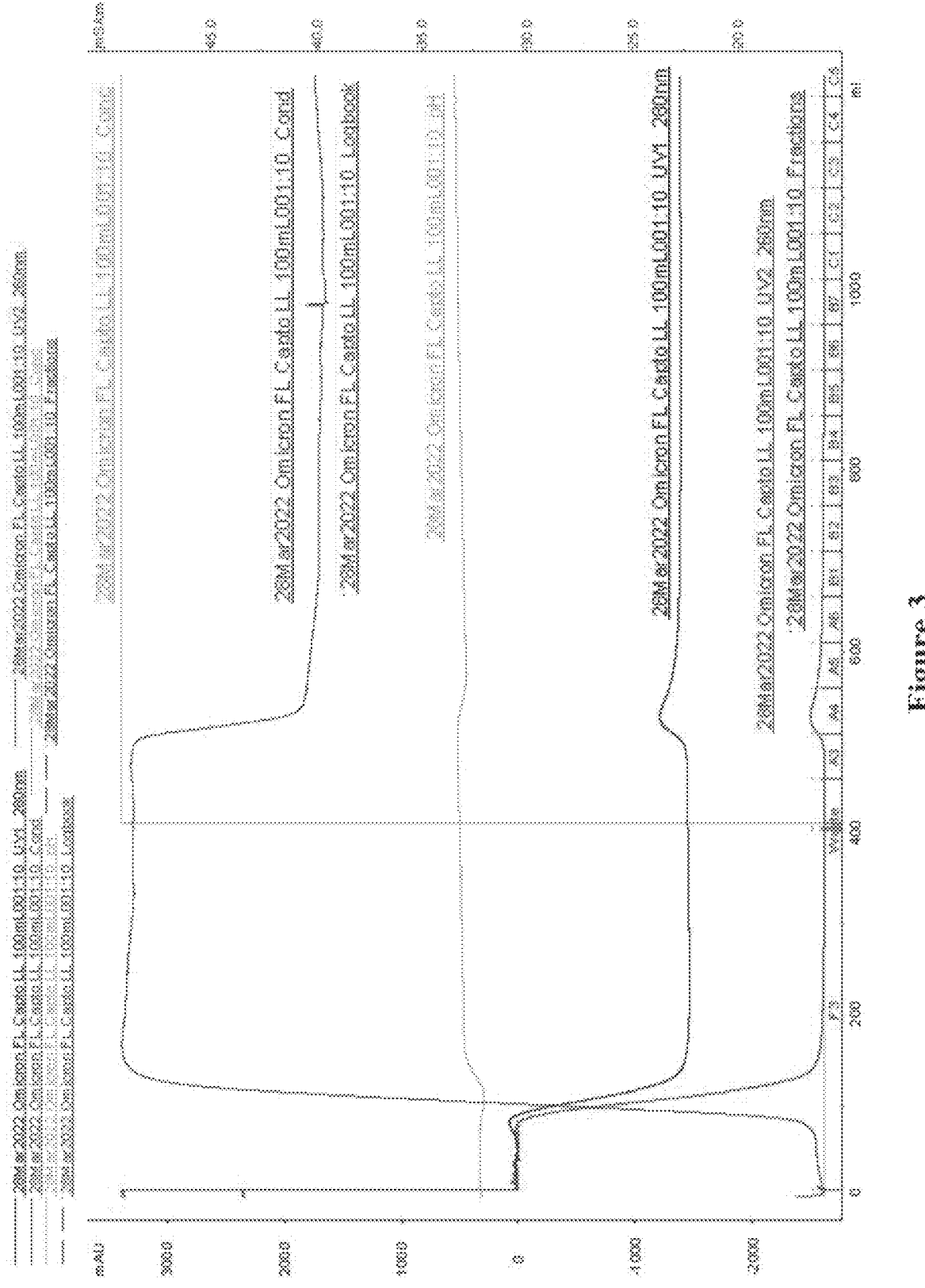

B. Purification of Modified Full-Length Spike Glycoprotein of Omicron BA.1 (SEQ ID. No. 3) from Culture Supernatant Purification of the modified full length spike protein of Omicron BA.1 (SEQ ID NO. 3) from culture supernatant was carried out according to the following process:

1. Passing the clarified cell culture supernatant containing the modified full length spike protein of Omicron BA.1 (6 liters) through affinity chromatography resin (100 mL Capto™ Lentil Lectin column). FIGS. 1-3 show the resulting solution after this step for three samples, as characterized by Akta Explorer FLPC System.

Parameters:

| | |
|---|---|
| Column Dimensions | 50 mm (d) × 5.0 cm (h) |
| Load Flow Rate | 25 mL/minute (75 cm/hr) |
| Wash Flow Rate | 25 mL/minute (75 cm/hr) |
| Elution Flow Rate | 25 mL/minute (75 cm/hr) |
| Column Equilibration | 5 cvs of Buffer A |
| Load | 4.5 L of mFL C1:2•6His cell culture supernatant |
| Wash | 5 cvs Buffer A11 |
| Elution | 10 cv step elution @100% B1 |
| Fraction Size | 50 mL |

Figure 4:
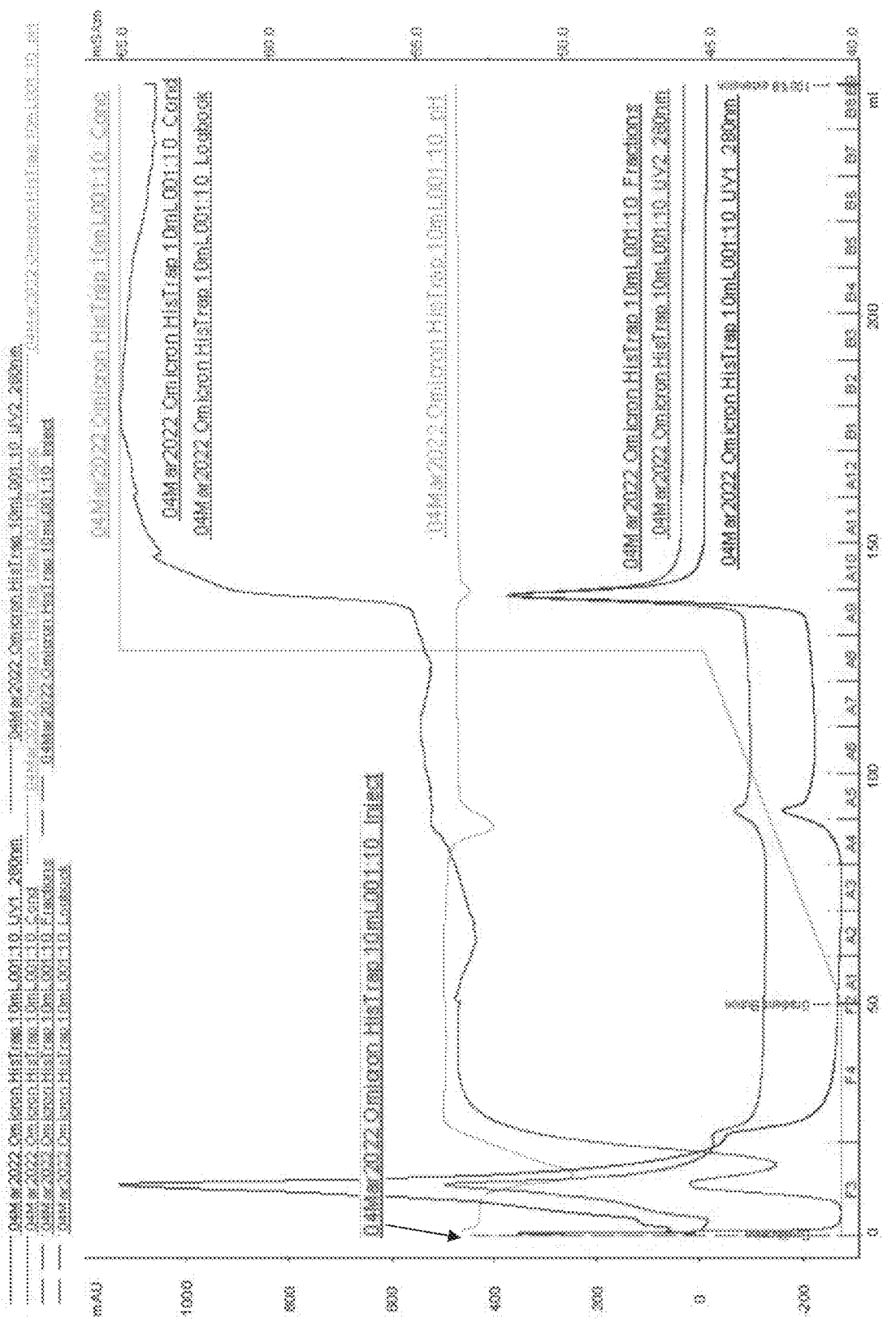
FIGS. 4, 5 and 6 depict chromatography graphs of the resulting solutions from purification of clarified cell culture supernatant containing the modified full length spike protein of Omicron BA.1 (SEQ. ID No. 3) with affinity chromatography resin and subsequent exposure to HisTrap™ columns. The chromatography graphs were obtained at 0 days (FIG. 4), 13 days (FIG. 5) and 27 days (FIG. 6).
Figure 5:
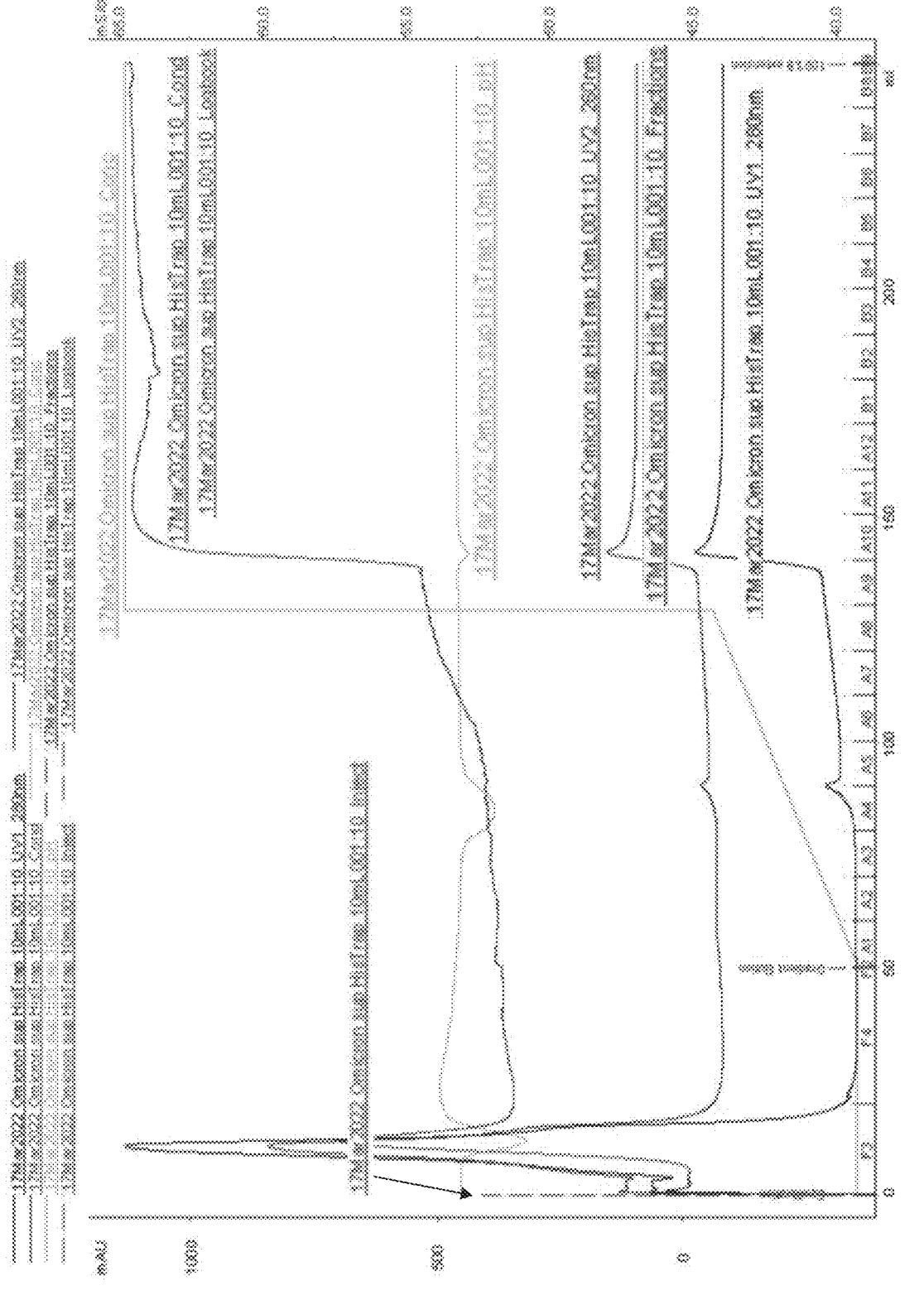
Figure 6:
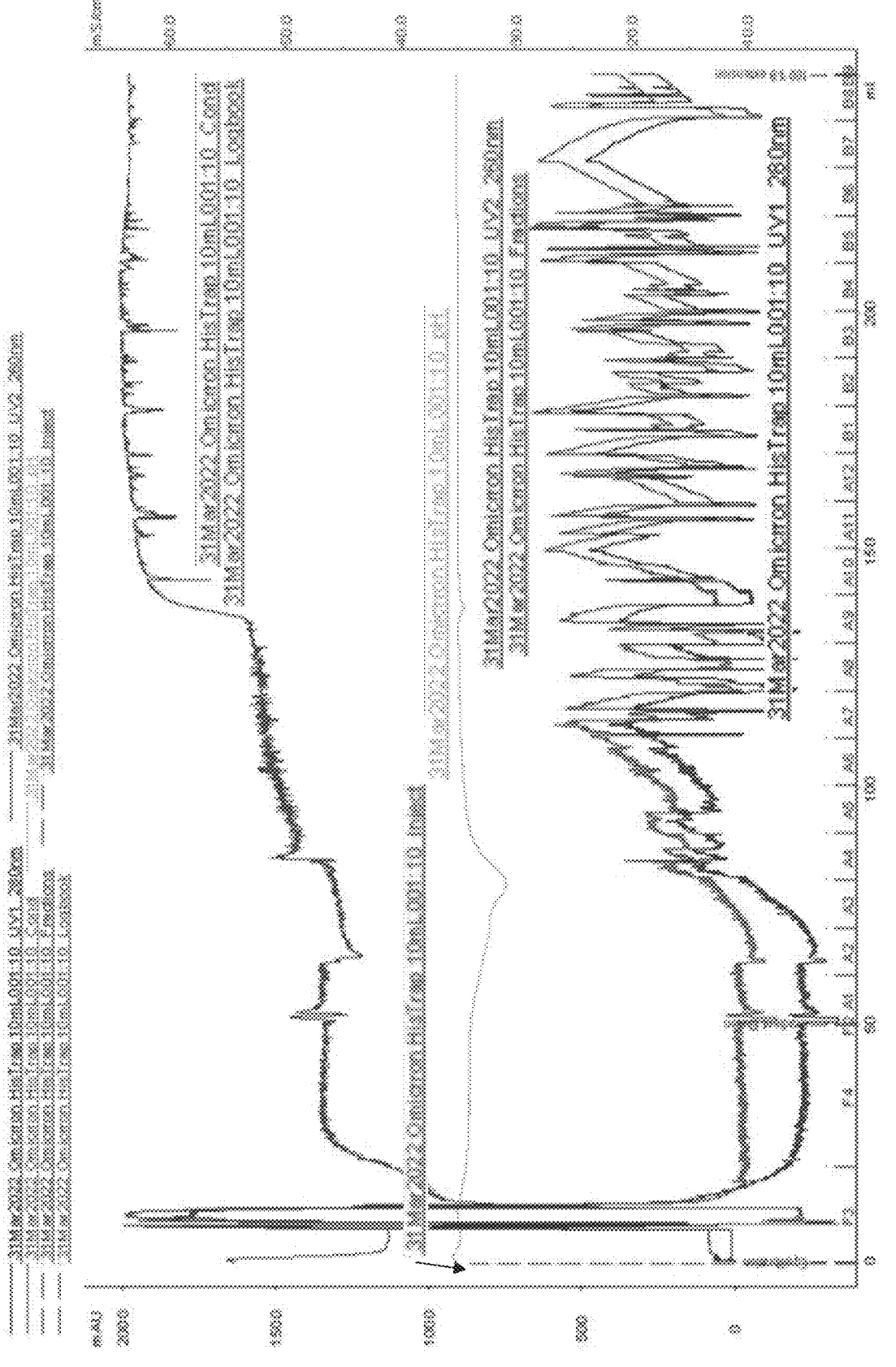
Figure 7:
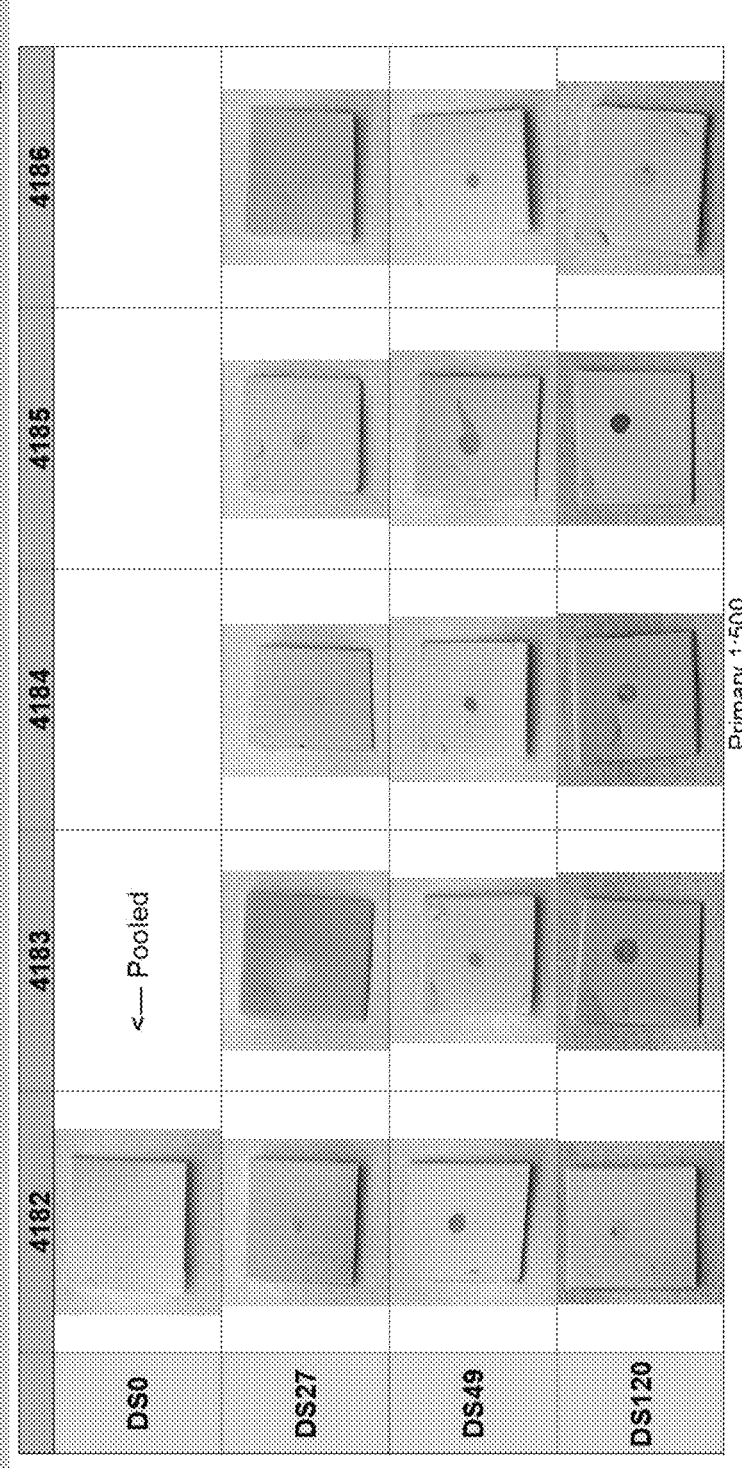
FIG. 7 depicts blot images for IgG antibodies directed against the Sino Wuhan Antigen full-length Spike protein of the SARS-COV-2. The animals were subcutaneously immunized with a SVE52 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. High antibody responses by blot were noted in all five animals at days 49 and 120. All five animals generated antibodies to the Sino Wuhan Spike Antigen at days 49 and 120.
Figure 8:
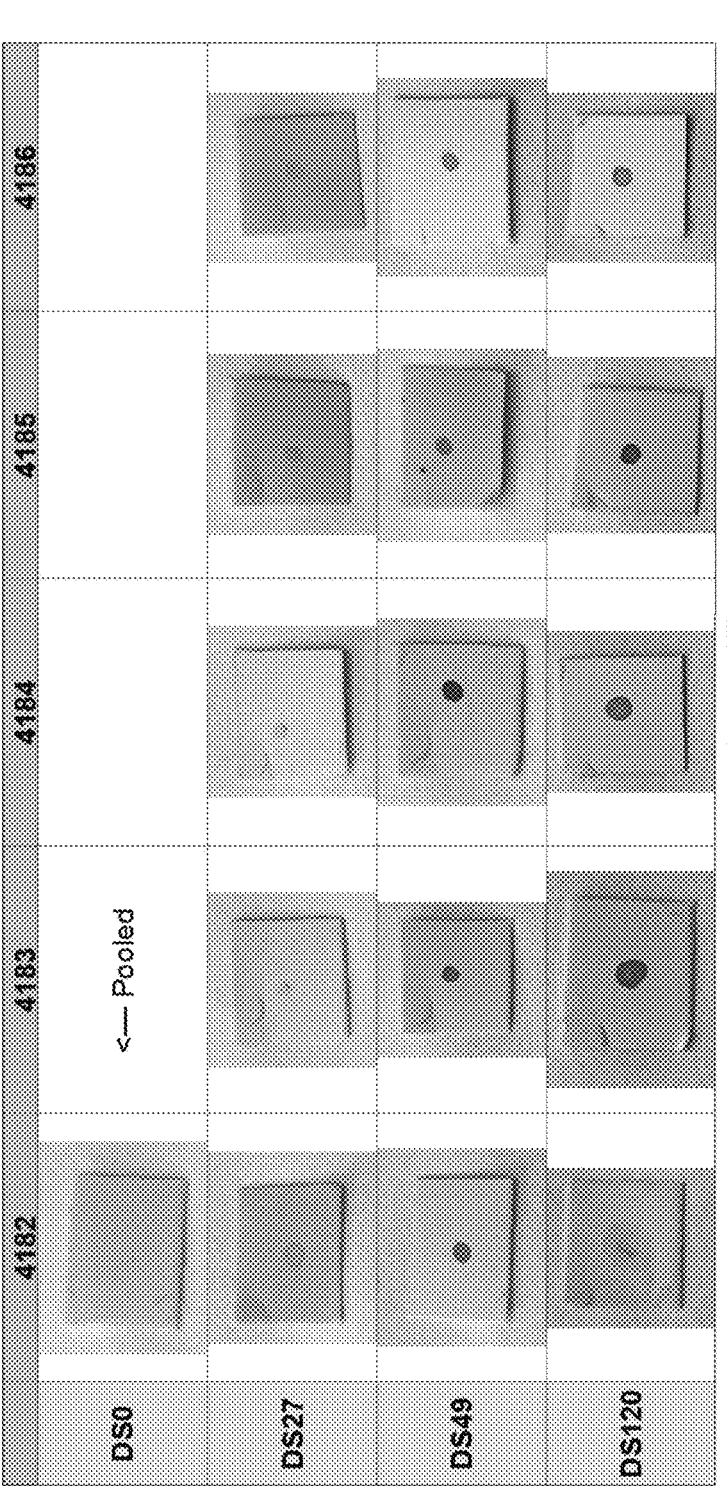
FIG. 8 depicts blot images for IgG antibodies directed against the Sino Delta Antigen full-length Spike protein of the SARS-COV-2. The animals were subcutaneously immunized with a SVE52 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. High antibody responses by blot were noted in all five animals at days 49 and 120. All five animals generated antibodies to the Sino Delta Spike Antigen at days 49 and 120.
Figure 9:
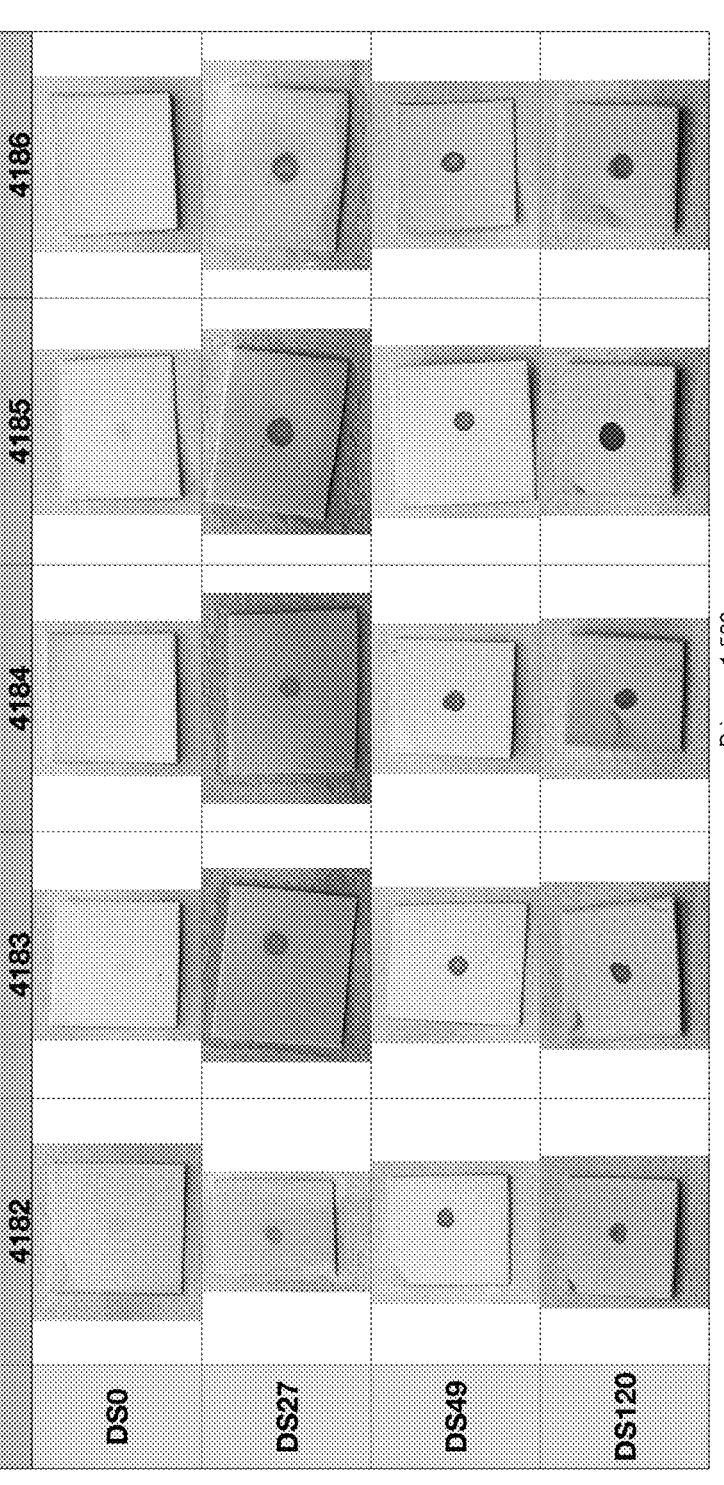
FIG. 9 depicts blot images for IgG antibodies directed against the Sino Omicron Antigen full-length Spike protein of the SARS-COV-2. The animals were subcutaneously immunized with a SVE52 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. High antibody responses by blot were noted in all five animals at days 49 and 120. All five animals generated antibodies to the Sino Omicron Spike Antigen at days 27, 49, and 120.
Figure 10:
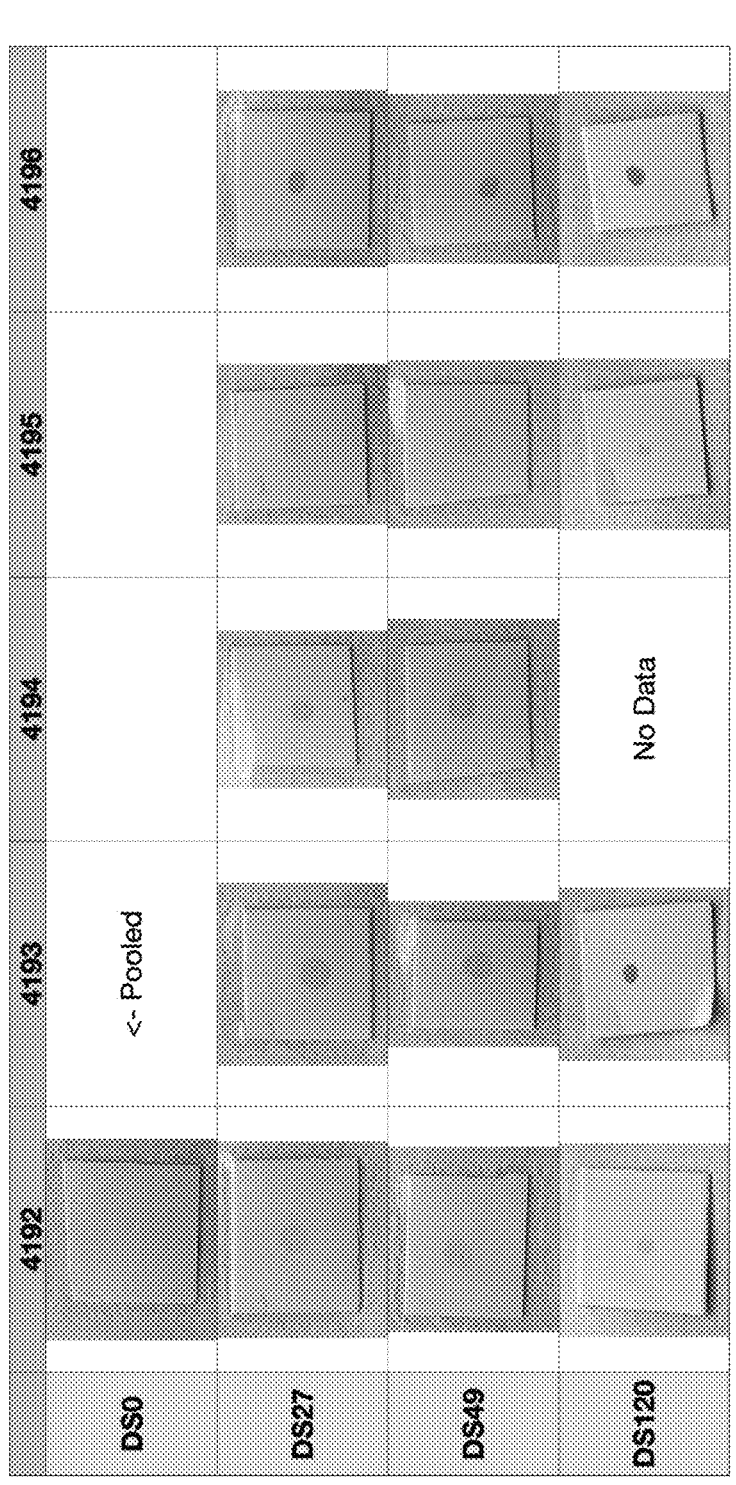
FIG. 10 depicts blot images for IgG antibodies directed against the Sino Wuhan Antigen full-length Spike protein of the SARS-COV-2. The animals were immunized intramuscularly with a SVE52 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. Strong antibody responses to the Sino Wuhan Spike Antigen by blot were noted in only two animals at day 120.
Figure 11:
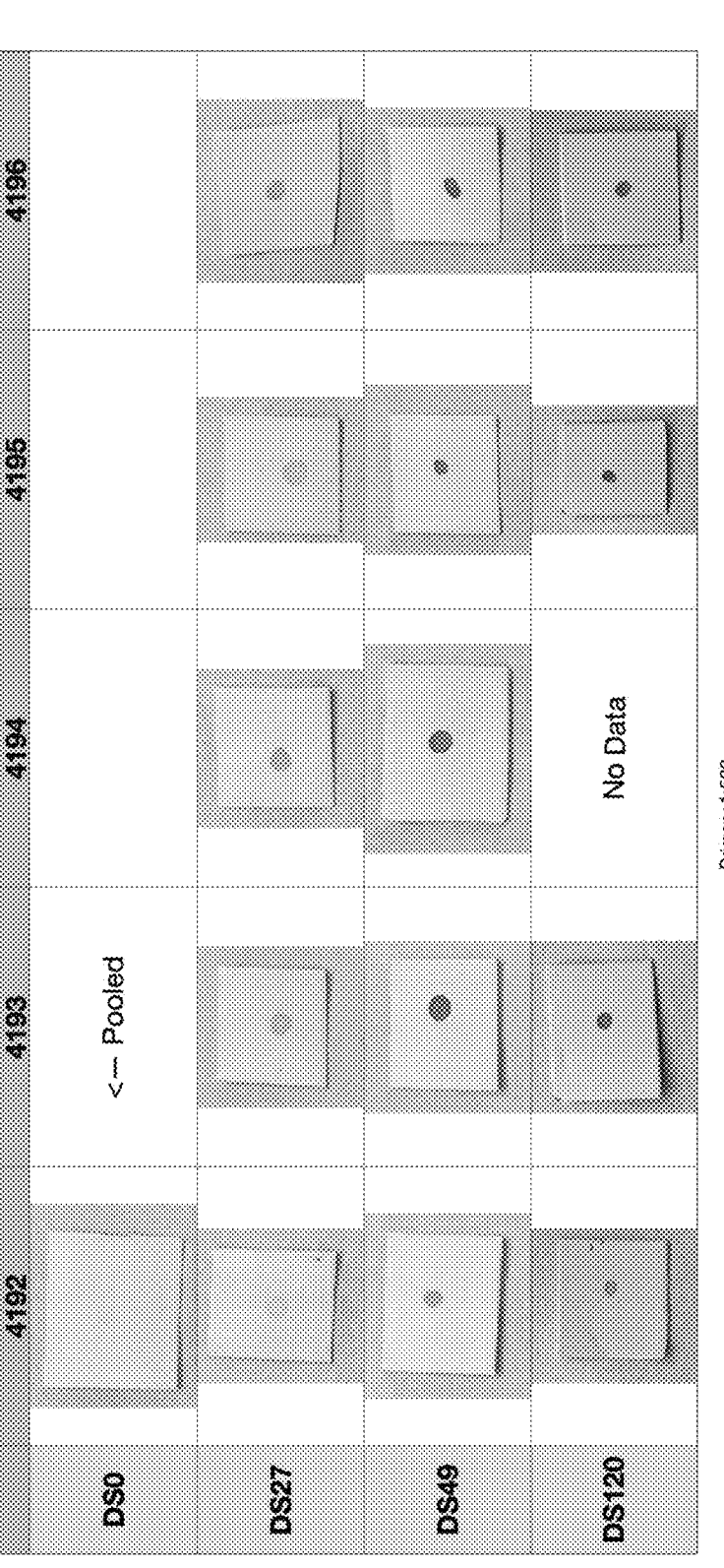
FIG. 11 depicts blot images for IgG antibodies directed against the Sino Delta Antigen full-length Spike protein of the SARS-COV-2. The animals were immunized intramuscularly with a SVE52 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. High antibody responses by blot were noted in all five animals at days 49 and 120. Strong antibody responses to the Sino Delta Spike Antigen were noted in all animals tested at day 49 and 120.
Figure 13:
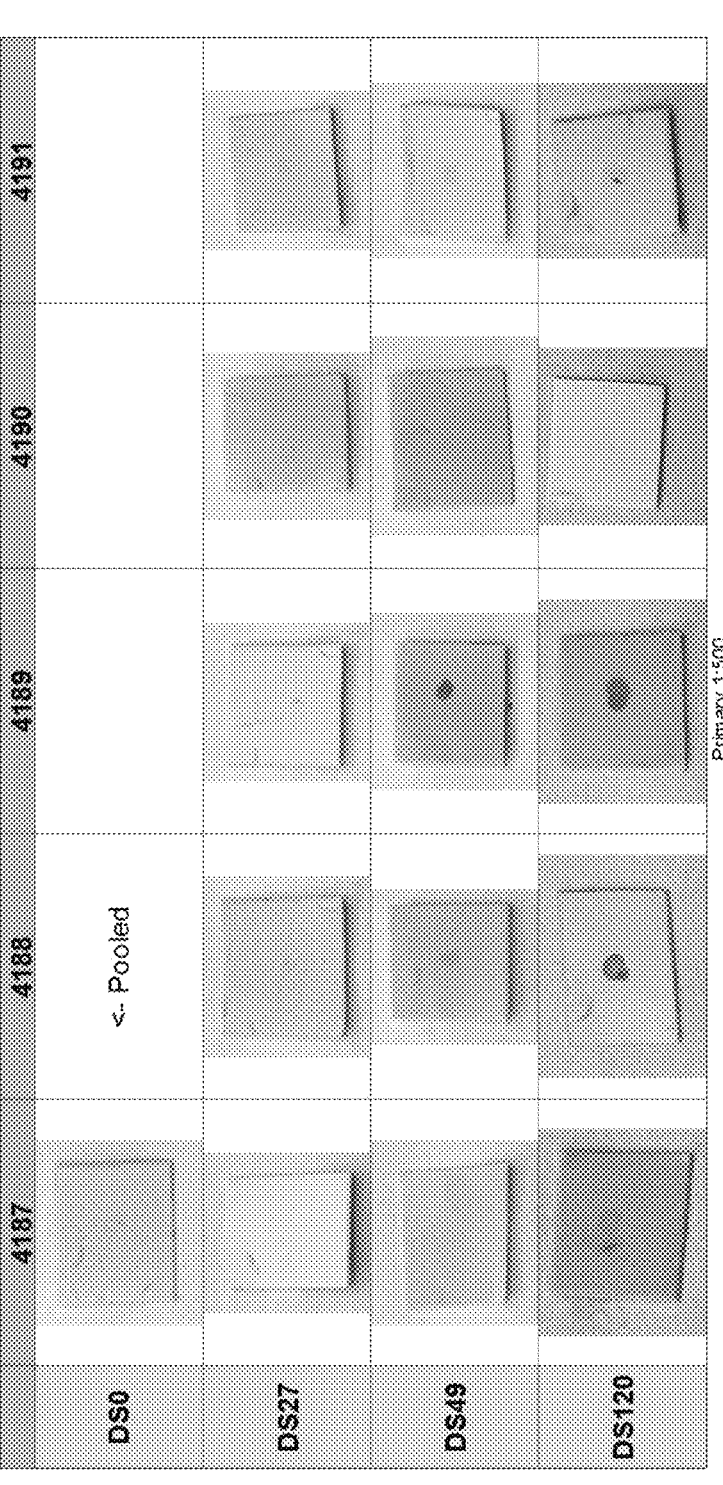
FIG. 13 depicts blot images for IgG antibodies directed against the Sino Wuhan Antigen full-length Spike protein of the SARS-COV-2. The animals were subcutaneously immunized with a SVE72 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. Antibody responses by blot to the Sino Wuhan Spike Antigen were noted in two of five animals at day 120.
Figure 15:
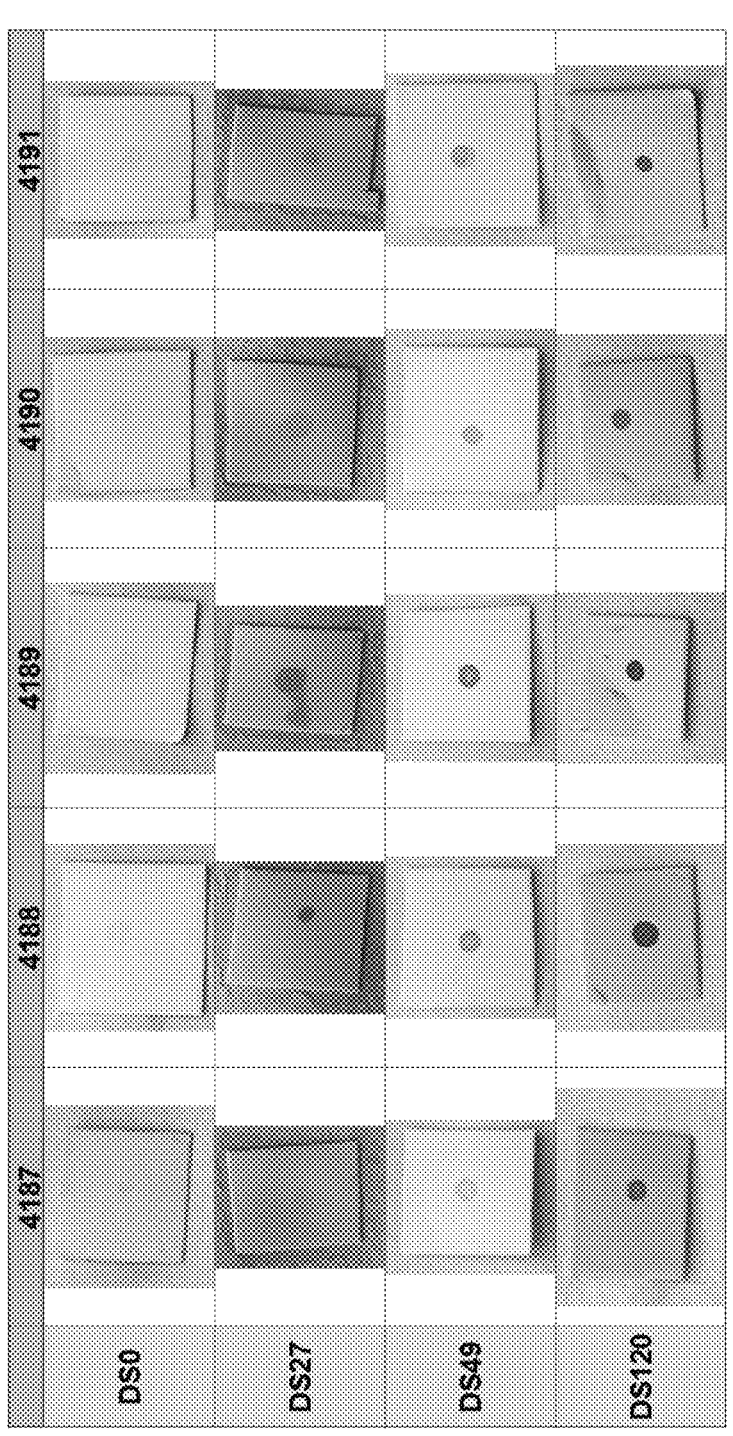
FIG. 15 depicts blot images for IgG antibodies directed against the Sino Omicron Antigen full-length Spike protein of the SARS-COV-2. The animals were subcutaneously immunized with a SVE72 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. Antibody responses by blot to the Sino Omicron Spike Antigen were noted in four of five animals at day 27 and five of five animals at days 49 and 120.
Figure 16:
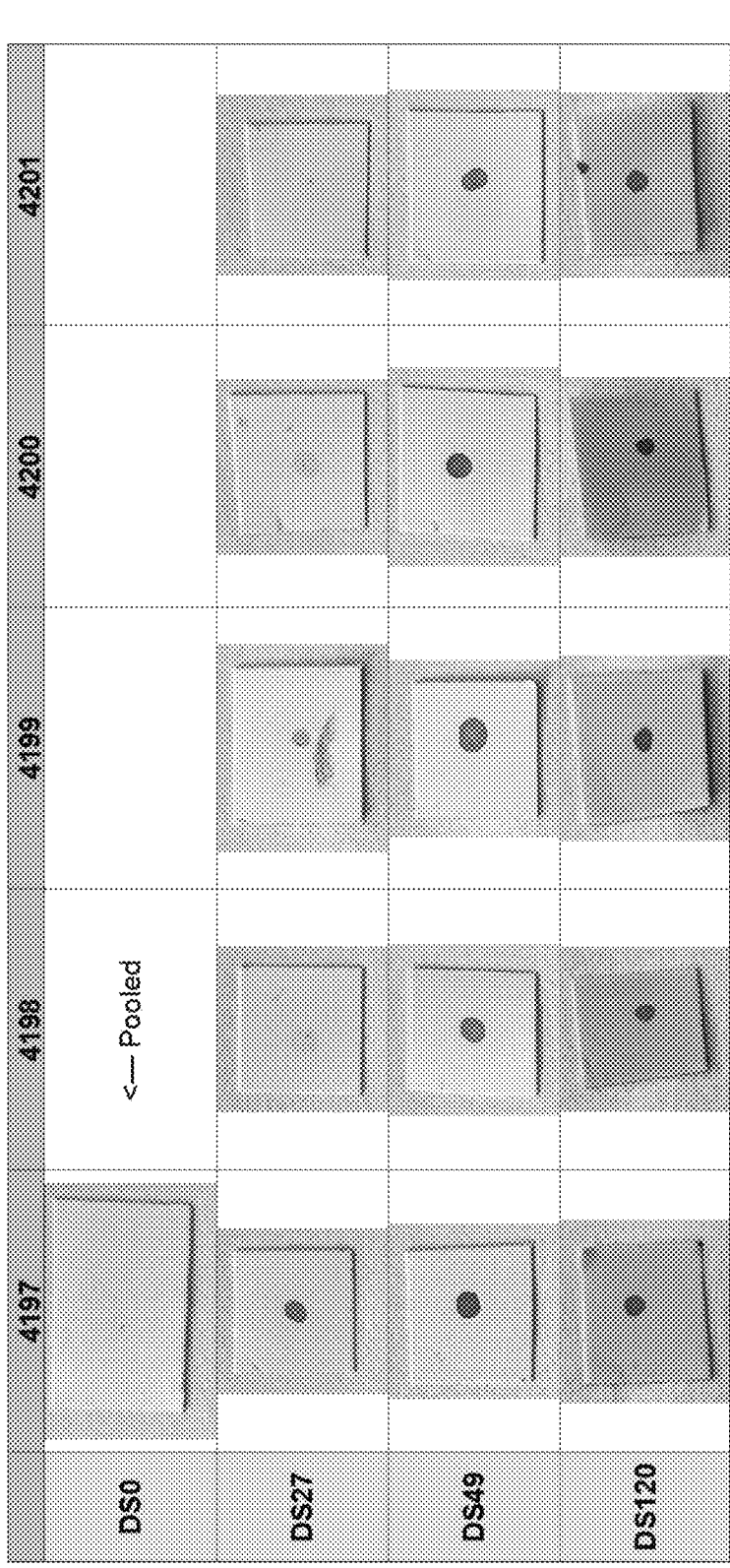
FIG. 16 depicts blot images for IgG antibodies directed against the Sino Wuhan Antigen full-length Spike protein of the SARS-COV-2. The animals were immunized intramuscularly with a SVE72 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. Antibody responses by blot to the Sino Wuhan Spike Antigen were noted in two of five animals at day 27 and five of five animals at days 49 and 120.
Figure 18:
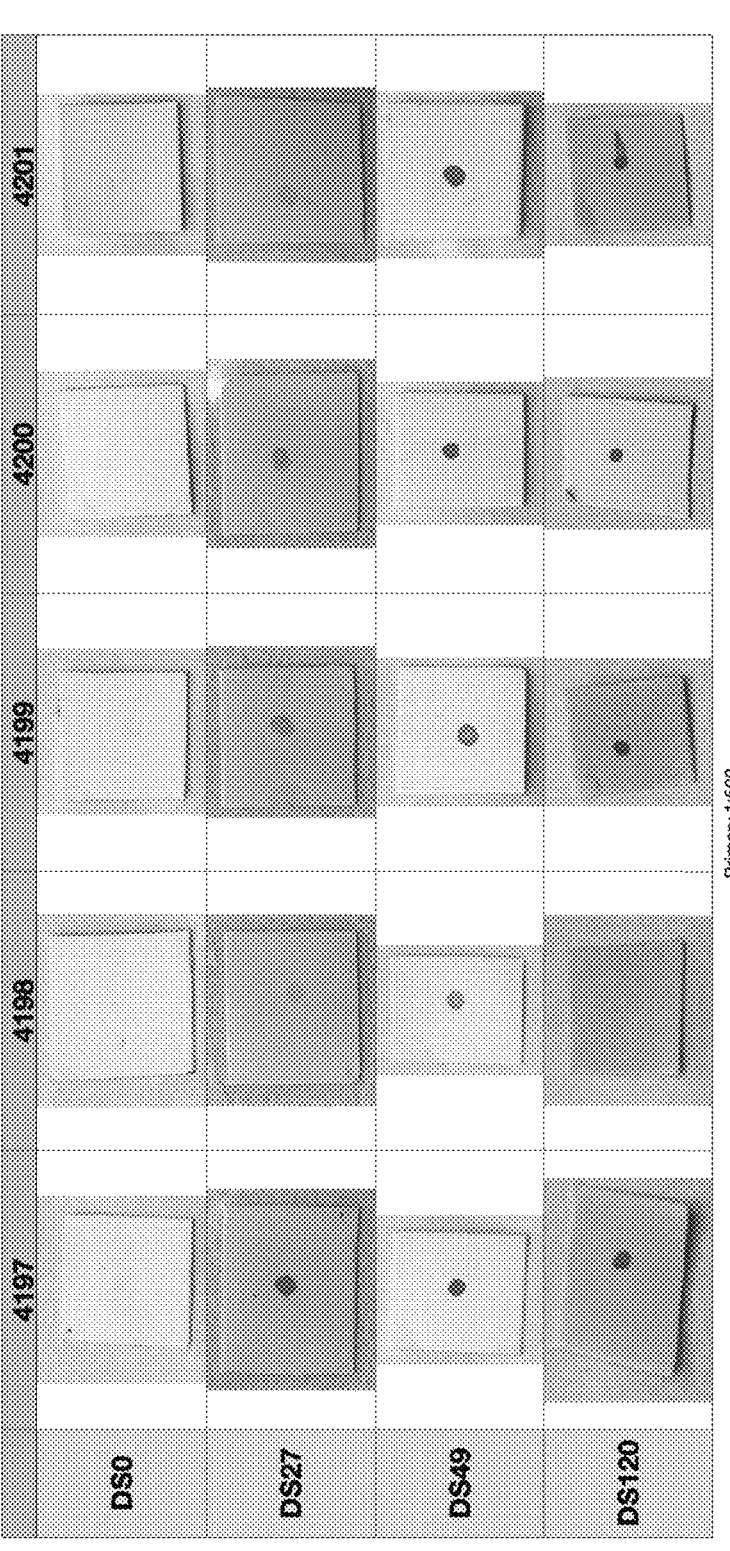
FIG. 18 depicts blot images for IgG antibodies directed against the Sino Omicron Antigen full-length Spike protein of the SARS-COV-2. The animals were immunized intramuscularly with a SVE72 non-phospholipid liposome containing vitamin E and a modified full-length sequence of the Omicron BA.1 variant of SARS-COV-2 (SEQ. ID No. 3). Animals were bled at days 0, 27, 49, and 120. Animals were immunized on days 1 and 28. The dilution of the sera was 1:500. Antibody responses by blot to the Sino Omicron Spike Antigen were noted in three of five animals at day 27, five of five at day 49, and four of five animals at day 120.
Figure 19:
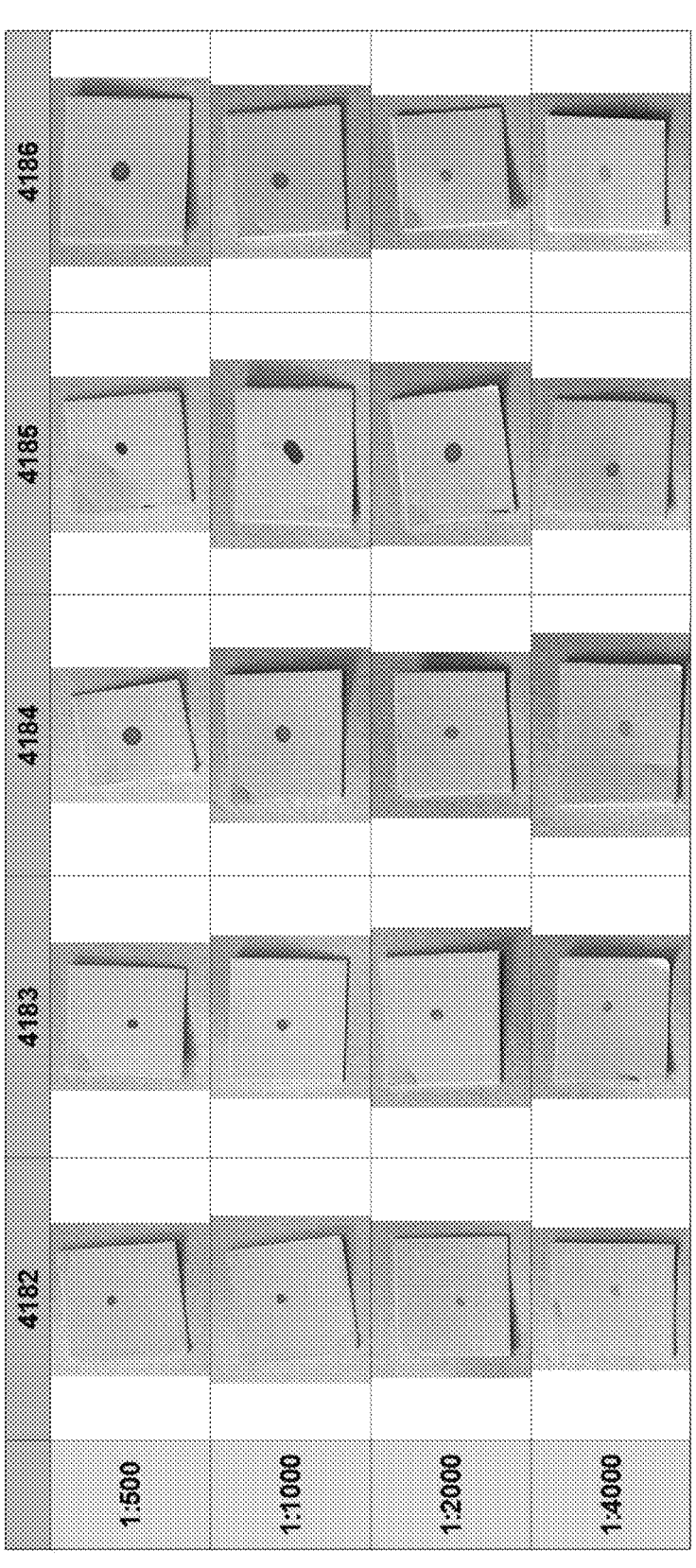
FIG. 19 depicts blot images for IgG antibodies directed against the Sino Omicron Antigen full-length Spike protein of the SARS-COV-2. The animals were immunized subcutaneously with a SVE52 non-phospholipid liposome containing vitamin E and a modified full-length sequence of the Omicron BA.1 variant of SARS-COV-2 (SEQ. ID No. 3). The day 120 bleed was tested in a serum dilution assay out to 1:4000. Five out of five animals were positive out to a dilution of sera at 1:2000.
Figure 22:
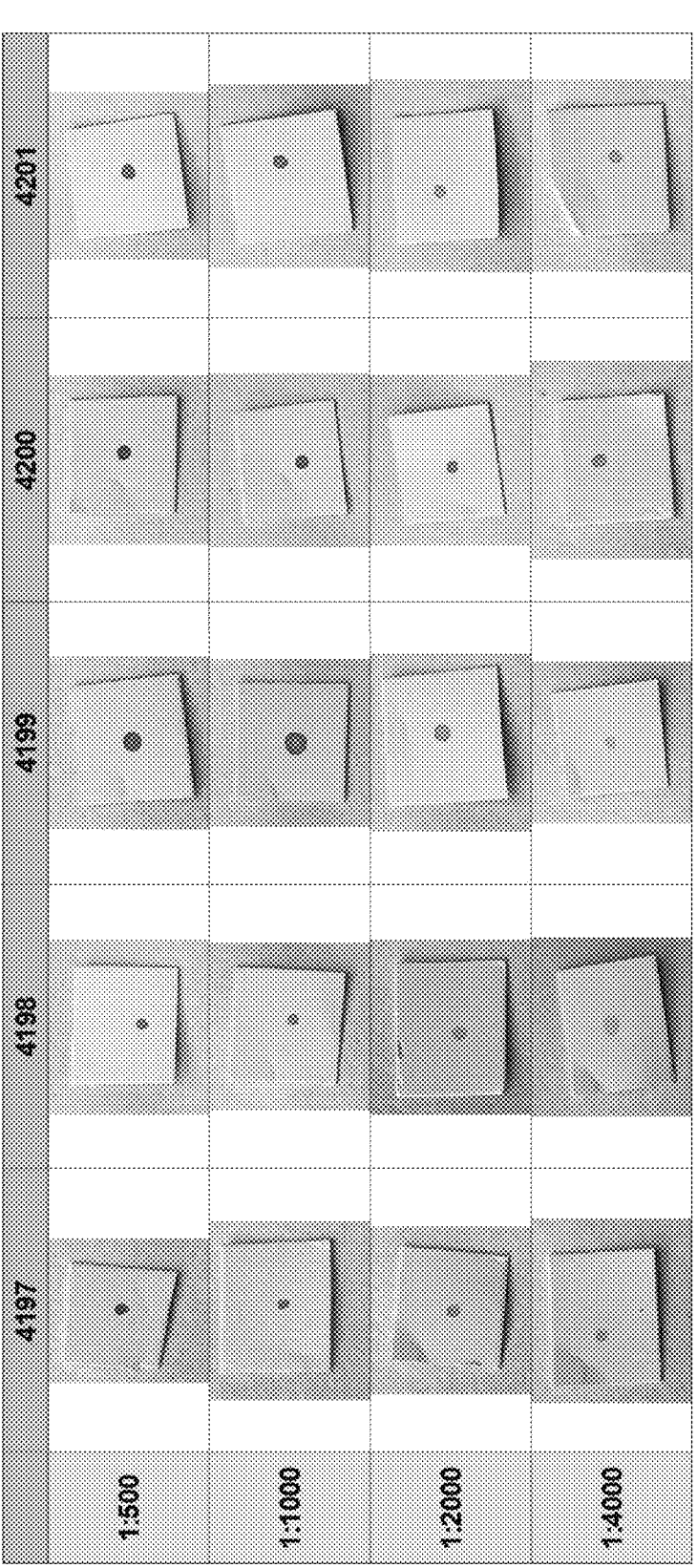
FIG. 22 depicts blot images for IgG antibodies directed against the Sino Omicron Antigen full-length Spike protein of the SARS-COV-2. The animals were immunized subcutaneously with a SVE72 non-phospholipid liposome containing vitamin E and a modified full-length sequence of the Omicron BA.1 variant of SARS-COV-2 (SEQ. ID No. 3). The day 120 bleed was tested in a serum dilution assay out to 1:4000. Five out of five animals were positive out to a dilution of sera at 1:4000.

2. Passing the resulting solution through two HisTrap™ 5 mL columns (10 mL total). A step elution to 100% B from 19% B to elute second product species more sharply was manually programmed. FIGS. 4-6 show the resulting solution after this step for three samples, as characterized by Akta Explorer FLPC System.

Parameters:

| | |
|---|---|
| Load Flow Rate | 5 mL/minute (150 cm/hr) |
| Wash Flow Rate | 5 mL/minute (150 cm/hr) |
| Elution Flow Rate | 5 mL/minute (150 cm/hr) |
| Column Equilibration | 5 cvs of Buffer A |
| Load | mFL C1:2 capto LL 100 mL elution fxns A3-A6, B1-B7, C1-C2 (650 mL pool) |
| Wash | 3 cvs Buffer A11 |
| Elution | 20 cv gradient elution to 50% B (manually programmed step to 100% B at 19% B) |
| Fraction Size | 10 mL |

3. Dialysis of the resulting solution.

4. Filtration of the resulting solution to produce the purified modified full length spike protein of Omicron BA.1 (SEQ ID NO. 3).

The purified product can subsequently be separated in aliquots and packaged.

Example 2: Exemplary Vaccines and Immunizations

Syrian golden hamsters were immunized on day 1 and 28, with approximately 2 µg of protein in 350 µL of adjuvant. Groups of five animals were immunized subcutaneously on days 0 and 28. Serum was collected and data from IgG blots for days 0, 27, 48, and 120 bleeds are shown below. A nitrocellulose blot technique for proteins was developed and used in this study. The proteins were the spike proteins of 2019 Wuhan Hu-1, Delta, and Omicron BA.1 variants of SARS-COV-2. These proteins were utilized to detect IgG antibodies in groups of five animals immunized with the vaccine.

All animals were immunized subcutaneously or intramuscularly. FIGS. 1, 2, and 3 show the bleed test data. Blot images show IgG antibodies directed against the spike proteins of 2019 Wuhan Hu-1, Delta, and Omicron BA.1 variants of SARS-COV-2.

The adjuvant formulations used for the above experiments were prepared using a reciprocating syringe technique which produced 5 milliliters of adjuvanted protein vaccine.

The liposome formulations were composed of polyoxy-ethylene-2-stearyl-ether (28.10 g), cholesterol (10.8 g), Vitamin E (5.4 g), and oleic acid (120 µl) (SVE52), or poly-oxyethylene-2-cetyl-ether (30.01 g), cholesterol (12.80 g), Vitamin E (6.00 g), and oleic acid (125 µl) (SVE72). The above chemicals are heated and then mixed by reciprocating syringe with protein solubilized in water. Other methods for manufacture include rotor stator emulsion technology and single pass continuous flow technology.

SVE are the initials for the Vitamin E-containing non-phospholipid-based liposome adjuvant.

Protein was solubilized in sterile water for injection at a concentration of 1.25 mg/mL. The lipid to diluent ratio on mixing was 1:4 on a volume basis. The final concentration of protein in the adjuvanted vaccine was approximately 2.0 µg protein in 350 µL of adjuvant.

Particle sizing of the exemplary vaccines was obtained via Beckman Coulter Laser Sizer LS 13 320 XR for initial samples (T1) and also samples aged 7 or 8 months (T2), as indicated below.

Table 1 provides particle sizing results for vaccines SVE52.SA.O.BA.1.MFLp SC from two lots of vaccine production corresponding to the immunization on DS1 (Lot #022222) and the immunization on DS28 (Lot #032222). Lot #022222 sizing was done initially and eight months later. Lot #032222 sizing was done initially and seven months later. 200 µL of sample was diluted into 10.0 mL dH2O, loaded onto the device until the target quantity reached 6-8% and the size was measured. Data is reported as an average of two runs in nm and the percent change reported shows product stability with a change in size of <10%.

TABLE 1

| Sizing SVE52.SA.O.BA.1.MFLp SC Lots 022222 and 032222 | | | | | |
|---|---|---|---|---|---|
| Product | Lot | Size (nm) T1 | Size (nm) T2 | Change in Size (nM) T2 – T1 | % Change |
| SVE52.SA.O.BA.1.MFLp SC | 022222 | 918.0 | 910.0 | –6.0 Decrease | 0.7 |
| SVE52.SA.O.BA.1.MFLp SC | 032222 | 869.0 | 876.0 | 7.0 Increase | 0.8 |

Table 2 provides particle sizing results for vaccines SVE52.SA.O.BA.1.MFLp IM from two lots of vaccine production corresponding to the immunization on DS1 (Lot #022222) and the immunization on DS28 (Lot #032222). Lot #022222 sizing was done initially and eight months later. Lot #032222 sizing was done on initially and seven months later. 200 µL of sample was diluted into 10.0 mL dH2O, loaded onto the device until the target quantity reached 6-8% and the size was measured. Data is reported as an average of two runs in nm and the percent change reported shows product stability with a change in size of <10%.

TABLE 2

| Sizing SVE52.SA.O.BA.1.MFLp IM Lots 022222 and 032222 | | | | | |
|---|---|---|---|---|---|
| Product | Lot | Size (nm) T1 | Size (nm) T2 | Change in Size (nM) T2 – T1 | % Change |
| SVE52.SA.O.BA.1.MFLp IM | 022222 | 1034.0 | 999.0 | –35.0 Decrease | 3.4 |
| SVE52.SA.O.BA.1.MFLp IM | 032222 | 912.0 | 1048.0 | 136.0 Increase | 14.9 |

Table 3 provides particle sizing results for vaccines SVE72.SA.O.BA.1.MFLp, SC from two lots of vaccine production corresponding to the immunization on DS1 (Lot #022222) and the immunization on DS28 (Lot #032222). Lot #022222 sizing was done initially and eight months later. Lot #032222 sizing was done initially and seven months later. 200 µL of sample was diluted into 10.0 mL dH2O, loaded onto the device until the target quantity reached 6-8% and the size was measured. Data is reported as an average of two runs in nm and the percent change reported shows product stability with a change in size of <10%.

TABLE 3

| Sizing SVE72.SA.O.BA.1.MFLp SC Lots 022222 and 032222 | | | | | |
|---|---|---|---|---|---|
| Product | Lot | Size (nm) T1 | Size (nm) T2 | Change in Size (nM) T2 – T1 | % Change |
| SVE72.SA.O.BA.1.MFLp SC | 022222 | 953.0 | 782.0 | –94.0 Decrease | 9.9 |
| SVE72.SA.O.BA.1.MFLp SC | 032222 | 935.0 | 1003.0 | 68.0 Increase | 7.3 |

Table 4 provides particle sizing results for vaccines Sizing SVE72.SA.O.BA.1.MFLp IM from two lots of vaccine production corresponding to the immunization on DS1 (Lot #022222) and the immunization on DS28 (Lot #032222). Lot #022222 sizing was done initially and eight months later. Lot #032222 sizing was done initially and seven months later. 200 μL of sample was diluted into 10.0 mL dH2O, loaded onto the device until the target quantity reached 6-8% and the size was measured. Data is reported as an average of two runs in nm and the percent change reported shows product stability with a change in size of <10%.

TABLE 4

| Sizing SVE72.SA.O.BA.1.MFLp IM Lots 022222 and 032222 | | | | | |
|---|---|---|---|---|---|
| Product | Lot | Size (nm) T1 | Size (nm) T2 | Change in Size (nM) T2 – T1 | % Change |
| SVE72.SA.O.BA.1.MFLp IM | 022222 | 1061.0 | 782.0 | –279.0 Decrease | 26.3 |
| SVE72.SA.O.BA.1.MFLp IM | 032222 | 977.0 | 978.0 | 1.0 Increase | 0.1 |

```
Sequence Listing
SARS-CoV-2 mutations from new variant B.1.1.529
Omicron 71 isolates in South Africa Nov. 11, 2021
superimposed on the surface glycoprotein [SARS-
CoV-2, China, Human Isolate, 2/18/20]: QJG65958.1
                                          Sequence ID No. 1
    1 mfvflvllpl vssqcvnltt rtqlppaytn sftrgvyypd kvfrssvlhs tqdlflpffs 61 nvtwfhvisg tngtkrfdnp vlpfndgvyf asieksniir gwifgttlds ktqsllivnn 121 atnvvikvce fqfcndpfld hknnkswmes efrvyssann ctfeyvsqpf lmdlegkqgn 181 fknlrefvfk nidgyfkiys khtpiivepe rdlpqgfsal eplvdlpigi nitrfqtlla 241 lhrsyltpgd sssgwtagaa ayyvgylqpm tyilkyneng titdavdcal dplsetkctl 301 ksftvekgiy qtsnfrvqpt esivrfpnit nlcpfdevin atrfasvyaw nrkrisncva 361 dysvlynlap fftfkcygvs ptklndlcft nvyadsfvir gdevrqiapg qtgniadyny 421 klpddftgcv iawnsnklds kvsgnynyly rlfrksnlkp ferdisteiy qagnkpcngv 481 agfncyfplk sysfrptygv ghqpyrvvvl sfellhapat vcgpkkstnl vknkcvnfnf 541 nglkgtgvlt esnkkflpfq qfgrdiadtt davrdpqtle ilditpcsfg gvsvitpgtn 601 tsnqvavlyq gvnctevpva ihadqltptw rvystgsnvf qtragcliga eyvnnsyecd 661 ipigagicas yqtqtkshrr arsvasqsii aytmslgaen svaysnnsia ipnnftisvt 721 teilpvsmtk tsvdctmyic gdstecinll lqygsfctql kraltgiave qdkntgevfa 781 qvkqiyktpp ikyfggfnfs qilpdpskps krsfiedllf nkvtladagf ikqygdclgd 841 iaardlicaq kfkgltvlpp lltdemiaqy tsallagtit sgwtfgagaa lqipfamqma 901 yrfngigvtq nvlyenqkli anqfnsaigk iqdslsstas algklqdvvn hnaqalntlv 961 kqlsskfgai ssvlndifsr ldkveaevqi drlitgrlqs lqtyvtqqli raaeirasan 1021 laatkmsecv lgqskrvdfc gkgyhlmsfp qsaphgvvfl hvtyvpagek nfttapaich 1081 dgkahfpreg vfvsngthwf vtqrnfyepq iittdntfvs gncdvvigiv nntvydplqp 1141 eldsfkeeld kyfknhtspd vdlgdisgin asvvniqkei drlnevaknl neslidlqel 1201 gkyegyikwp wyiwlgfiag liaivmvtim lccmtsccsc lkgccscgsc ckfdeddsep
```

-continued 1261 vlkgvklhyt

Modified BA.1 sequence with 163 amino acids removed
at the C terminus of the protein.

Sequence ID No. 2

1 mfvflvllpl vssqcvnltt rtqlppaytn sftrgvyypd kvfrssvlhs tqdlflpffs 61 nvtwfhvisg tngtkrfdnp vlpfndgvyf asieksniir gwifgttlds ktqsllivnn 121 atnvvikvce fqfcndpfld hknnkswmes efrvyssann ctfeyvsqpf lmdlegkqgn 181 fknlrefvfk nidgyfkiys khtpiivepe rdlpqgfsal eplvdlpigi nitrfqtlla 241 lhrsyltpgd sssgwtagaa ayyvgylqpm tyilkyneng titdavdcal dplsetkctl 301 ksftvekgiy qtsnfrvqpt esivrfpnit nlcpfdevin atrfasvyaw nrkrisncva 361 dysvlynlap fftfkcygvs ptklndlcft nvyadsfvir gdevrqiapg qtgniadyny 421 klpddftgcv iawnsnklds kvsgnynyly rlfrksnlkp ferdisteiy qagnkpcngv 481 agfncyfplk sysfrptygv ghqpyrvvvl sfellhapat vcgpkkstnl vknkcvnfnf 541 nglkgtgvlt esnkkflpfq qfgrdiadtt davrdpqtle ilditpcsfg gvsvitpgtn 601 tsnqvavlyq gvnctevpva ihadqltptw rvystgsnvf qtragcliga eyvnnsyecd 661 ipigagicas yqtqtkshrr arsvasqsii aytmslgaen svaysnnsia ipnnftisvt 721 teilpvsmtk tsvdctmyic gdstecinll lqygsfctql kraltgiave qdkntqevfa 781 qvkqiyktpp ikyfggfnfs qilpdpskps krsfiedllf nkvtladagf ikqygdclgd 841 iaardlicaq kfkgltvlpp lltdemiaqy tsallagtit sgwtfgagaa lqipfamqma 901 yrfngigvtq nvlyenqkli anqfnsaigk iqdslsstas algklqdvvn hnaqalntlv 961 kqlsskfgai ssvlndifsr ldkveaevqi drlitgrlqs lqtyvtqqli raaeirasan 1021 laatkmsecv lgqskrvdfc gkgyhlmsfp qsaphgvvfl hvtyvpagek nfttapaich 1081 dgkahfpreg vfvsngthwf vtqrnfy Final construct is 1107 Amino Acids of the modified
Omicron BA.1 spike protein with an additional 11 amino
acid His-tag. His-tag is depicted below in black bolding
at the C terminus of the construct. The furin cleavage
site changes are also depicted in bold.

Sequence ID No. 3

MFVFLVLLPL VSSQCVNLTT RTQLPPAYTN SFTRGVYYPD KVFRSSVLHS TQDLFLPFFS

NVTWFHVISG TNGTKRFDNP VLPFNDGVYF ASIEKSNIIR GWIFGTTLDS KTQSLLIVNN

ATNVVIKVCE FQFCNDPFLD HKNNKSWMES EFRVYSSANN CTFEYVSQPF LMDLEGKQGN

FKNLREFVFK NIDGYFKIYS KHTPIIVEPE RDLPQGFSAL EPLVDLPIGI NITRFQTLLA

LHRSYLTPGD SSSGWTAGAA AYYVGYLQPM TYILKYNENG TITDAVDCAL DPLSETKCTL

KSFTVEKGIY QTSNERVQPT ESIVRFPNIT NLCPFDEVFN ATRFASVYAW NRKRISNCVA

DYSVLYNLAP FFTFKCYGVS PTKLNDLCFT NVYADSFVIR GDEVRQIAPG QTGNIADYNY

KLPDDFTGCV IAWNSNKLDS KVSGNYNYLY RLFRKSNLKP FERDISTEIY QAGNKPCNGV

AGFNCYFPLK SYSFRPTYGV GHQPYRVVVL SFELLHAPAT VCGPKKSTNL VKNKCVNFNF

NGLKGTGVLT ESNKKFLPFQ QFGRDIADTT DAVRDPQTLE ILDITPCSFG GVSVITPGTN

TSNQVAVLYQ GVNCTEVPVA IHADQLTPTW RVYSTGSNVF QTRAGCLIGA EYVNNSYECD

IPIGAGICAS YQTQTKSKKK AKSVASQSII AYTMSLGAEN SVAYSNNSIA IPNNFTISVT

TEILPVSMTK TSVDCTMYIC GDSTECINLL LQYGSFCTQL KRALTGIAVE QDKNTQEVFA

QVKQTYKTPP IKYFGGFNFS QILPDPSKPS KRSFIEDLLF NKVTLADAGF IKQYGDCLGD

IAARDLICAQ KFKGLTVLPP LLTDEMIAQY TSALLAGTIT SGWTFGAGAA LQIPFAMQMA

YRFNGIGVTQ NVLYENQKLI ANQFNSAIGK IQDSLSSTAS ALGKLQDVVN HNAQALNTLV

-continued

KQLSSKFGAI SSVLNDIFSR LDKVEAEVQI DRLITGRLQS LQTYVTQQLI RAAEIRASAN

LAATKMSECV LGQSKRVDFC GKGYHLMSFP QSAPHGVVFL HVTYVPAQEK NFTTAPAICH

DGKAHFPREG VFVSNGTHWF VTQRNFYQGP GSHHHHHH

Sequence from the Omicron BA.1 spike protein
at amino acids 1228-1247.

Sequence ID. No. 4

VMTIMLCCMTSCCSCLKGC

Sequence found in keratin associated protein4-7
(KRTAP4-7) in human skin, which has
sequence homology to SEQ. ID. No. 4.

Sequence ID. No. 5

CCMSSCC

Sequence from Metallothionein 1 E (MTIE) found
in human liver and many other tissues, which has
sequence homology to SEQ. ID. No. 4.

Sequence ID. No. 6

CKTSCCSC

Sequence from the Omicron BA.1 spike protein
at amino acids 1186-1205.

Sequence ID. No. 7

LNEVAKNLNESLIDLQELGK

Sequence found in human Coiled-containing domain-
containing protein 175 isoform X8, which is found
in human brain, pituitary gland, and testis. This
sequence has sequence homology to SEQ. ID. No. 7.

Sequence ID. No. 8

KNMEEGLITLQEL

Sequence found in human hCG23535, which is found
in human brain. This sequence has sequence
homology to SEQ. ID. No. 7.

Sequence ID. No. 9

KNLNQSLLDLHALG

Sequence from the Omicron BA.1 spike protein at
amino acids 1149-1168.

Sequence ID. No. 10

KEELDKYFKNHTSPDVDLGD

Sequence found in Follistatin-related protein 1
isoform X1 in human placenta, which has
sequence homology to SEQ. ID. No. 10.

Sequence ID. No. 11

EILDKYFKN

Furin cleavage site sequence

Sequence ID. No. 12

HRRAR

Protease resistant sequence replacing furin
cleavage site sequence

Sequence ID. No. 13

KKKAK

His-tag sequence.

Sequence ID. No. 14

QGPSPHHHHHH

---

SEQUENCE LISTING

Sequence total quantity: 15
SEQ ID NO: 1          moltype = AA  length = 1270
FEATURE               Location/Qualifiers
source                1..1270
                      mol_type = protein
                      organism = Severe acute respiratory synthetic
                       constructdrome coronavirus 2
SEQUENCE: 1
MFVFLVLLPL VSSQCVNLTT RTQLPPAYTN SFTRGVYYPD KVFRSSVLHS TQDLFLPFFS  60
NVTWFHVISG TNGTKRFDNP VLPFNDGVYF ASIEKSNIIR GWIFGTTLDS KTQSLLIVNN  120

```
ATNVVIKVCE FQFCNDPFLD HKNNKSWMES EFRVYSSANN CTFEYVSQPF LMDLEGKQGN   180
FKNLREFVFK NIDGYFKIYS KHTPIIVEPE RDLPQGFSAL EPLVDLPIGI NITRFQTLLA   240
LHRSYLTPGD SSSGWTAGAA AYYVGYLQPM TYILKYNENG TITDAVDCAL DPLSETKCTL   300
KSFTVEKGIY QTSNFRVQPT ESIVRFPNIT NLCPFDEVFN ATRFASVYAW NRKRISNCVA   360
DYSVLYNLAP FFTFKCYGVS PTKLNDLCFT NVYADSFVIR GDEVRQIAPG QTGNIADYNY   420
KLPDDFTGCV IAWNSNKLDS KVSGNYNYLY RLFRKSNLKP FERDISTEIY QAGNKPCNGV   480
AGFNCYFPLK SYSFRPTYGV GHQPYRVVVL SFELLHAPAT VCGPKKSTNL VKNKCVNFNF   540
NGLKGTGVLT ESNKKFLPFQ QFGRDIADTT DAVRDPQTLE ILDITPCSFG GVSVITPGTN   600
TSNQVAVLYQ GVNCTEVPVA IHADQLTPTW RVYSTGSNVF QTRAGCLIGA EYVNNSYECD   660
IPIGAGICAS YQTQTKSHRR ARSVASQSII AYTMSLGAEN SVAYSNNSIA IPNNFTISVT   720
TEILPVSMTK TSVDCTMYIC GDSTECINLL LQYGSFCTQL KRALTGIAVE QDKNTQEVFA   780
QVKQIYKTPP IKYFGGFNFS QILPDPSKPS KRSFIEDLLF NKVTLADAGF IKQYGDCLGD   840
IAARDLICAQ KFKGLTVLPP LLTDEMIAQY TSALLAGTIT SGWTFGAGAA LQIPFAMQMA   900
YRFNGIGVTQ NVLYENQKLI ANQFNSAIGK IQDSLSSTAS ALGKLQDVVN HNAQALNTLV   960
KQLSSKFGAI SSVLNDIFSR LDKVEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                         1270

SEQ ID NO: 2            moltype = AA  length = 1107
FEATURE                 Location/Qualifiers
source                  1..1107
                        mol_type = protein
                        organism = synthetic construct
SEQUENCE: 2
MFVFLVLLPL VSSQCVNLTT RTQLPPAYTN SFTRGVYYPD KVFRSSVLHS TQDLFLPFFS   60
NVTWFHVISG TNGTKRFDNP VLPFNDGVYF ASIEKSNIIR GWIFGTTLDS KTQSLLIVNN  120
ATNVVIKVCE FQFCNDPFLD HKNNKSWMES EFRVYSSANN CTFEYVSQPF LMDLEGKQGN  180
FKNLREFVFK NIDGYFKIYS KHTPIIVEPE RDLPQGFSAL EPLVDLPIGI NITRFQTLLA  240
LHRSYLTPGD SSSGWTAGAA AYYVGYLQPM TYILKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNLAP FFTFKCYGVS PTKLNDLCFT NVYADSFVIR GDEVRQIAPG QTGNIADYNY  420
KLPDDFTGCV IAWNSNKLDS KVSGNYNYLY RLFRKSNLKP FERDISTEIY QAGNKPCNGV  480
AGFNCYFPLK SYSFRPTYGV GHQPYRVVVL SFELLHAPAT VCGPKKSTNL VKNKCVNFNF  540
NGLKGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSHRR ARSVASQSII AYTMSLGAEN SVAYSNNSIA IPNNFTISVT  720
TEILPVSMTK TSVDCTMYIC GDSTECINLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFKGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDIFSR LDKVEAEVQI DRLITGRLQS LQTYVTQQLI RAAEIRASAN 1020
LAATKMSECV LGQSKRVDFC GKGYHLMSFP QSAPHGVVFL HVTYVPAQEK NFTTAPAICH 1080
DGKAHFPREG VFVSNGTHWF VTQRNFY                                     1107

SEQ ID NO: 3            moltype = AA  length = 1118
FEATURE                 Location/Qualifiers
source                  1..1118
                        mol_type = protein
                        organism = synthetic construct
SEQUENCE: 3
MFVFLVLLPL VSSQCVNLTT RTQLPPAYTN SFTRGVYYPD KVFRSSVLHS TQDLFLPFFS   60
NVTWFHVISG TNGTKRFDNP VLPFNDGVYF ASIEKSNIIR GWIFGTTLDS KTQSLLIVNN  120
ATNVVIKVCE FQFCNDPFLD HKNNKSWMES EFRVYSSANN CTFEYVSQPF LMDLEGKQGN  180
FKNLREFVFK NIDGYFKIYS KHTPIIVEPE RDLPQGFSAL EPLVDLPIGI NITRFQTLLA  240
LHRSYLTPGD SSSGWTAGAA AYYVGYLQPM TYILKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNLAP FFTFKCYGVS PTKLNDLCFT NVYADSFVIR GDEVRQIAPG QTGNIADYNY  420
KLPDDFTGCV IAWNSNKLDS KVSGNYNYLY RLFRKSNLKP FERDISTEIY QAGNKPCNGV  480
AGFNCYFPLK SYSFRPTYGV GHQPYRVVVL SFELLHAPAT VCGPKKSTNL VKNKCVNFNF  540
NGLKGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSKKK AKSVASQSII AYTMSLGAEN SVAYSNNSIA IPNNFTISVT  720
TEILPVSMTK TSVDCTMYIC GDSTECINLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFKGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDIFSR LDKVEAEVQI DRLITGRLQS LQTYVTQQLI RAAEIRASAN 1020
LAATKMSECV LGQSKRVDFC GKGYHLMSFP QSAPHGVVFL HVTYVPAQEK NFTTAPAICH 1080
DGKAHFPREG VFVSNGTHWF VTQRNFYQGP GSHHHHHH                         1118

SEQ ID NO: 4            moltype = AA  length = 19
FEATURE                 Location/Qualifiers
source                  1..19
                        mol_type = protein
                        organism = Severe acute respiratory synthetic
                         constructdrome coronavirus 2
```

```
SEQUENCE: 4
VMTIMLCCMT SCCSCLKGC                                                        19

SEQ ID NO: 5            moltype = AA  length = 7
FEATURE                 Location/Qualifiers
source                  1..7
                        mol_type = protein
                        organism = Homo sapiens
SEQUENCE: 5
CCMSSCC                                                                      7

SEQ ID NO: 6            moltype = AA  length = 8
FEATURE                 Location/Qualifiers
source                  1..8
                        mol_type = protein
                        organism = Homo sapiens
SEQUENCE: 6
CKTSCCSC                                                                     8

SEQ ID NO: 7            moltype = AA  length = 20
FEATURE                 Location/Qualifiers
source                  1..20
                        mol_type = protein
                        organism = Severe acute respiratory synthetic
                         constructdrome coronavirus 2
SEQUENCE: 7
LNEVAKNLNE SLIDLQELGK                                                        20

SEQ ID NO: 8            moltype = AA  length = 13
FEATURE                 Location/Qualifiers
source                  1..13
                        mol_type = protein
                        organism = Homo sapiens
SEQUENCE: 8
KNMEEGLITL QEL                                                               13

SEQ ID NO: 9            moltype = AA  length = 14
FEATURE                 Location/Qualifiers
source                  1..14
                        mol_type = protein
                        organism = Homo sapiens
SEQUENCE: 9
KNLNQSLLDL HALG                                                              14

SEQ ID NO: 10           moltype = AA  length = 20
FEATURE                 Location/Qualifiers
source                  1..20
                        mol_type = protein
                        organism = Severe acute respiratory synthetic
                         constructdrome coronavirus 2
SEQUENCE: 10
KEELDKYFKN HTSPDVDLGD                                                        20

SEQ ID NO: 11           moltype = AA  length = 9
FEATURE                 Location/Qualifiers
source                  1..9
                        mol_type = protein
                        organism = Homo sapiens
SEQUENCE: 11
EILDKYFKN                                                                    9

SEQ ID NO: 12           moltype = AA  length = 5
FEATURE                 Location/Qualifiers
source                  1..5
                        mol_type = protein
                        organism = synthetic construct
SEQUENCE: 12
HRRAR                                                                        5

SEQ ID NO: 13           moltype = AA  length = 5
FEATURE                 Location/Qualifiers
source                  1..5
                        mol_type = protein
                        organism = synthetic construct
SEQUENCE: 13
KKKAK                                                                        5

SEQ ID NO: 14           moltype = AA  length = 11
FEATURE                 Location/Qualifiers
```

-continued

```
source                  1..11
                        mol_type = protein
                        organism = synthetic construct
SEQUENCE: 14
QGPSPHHHHH H                                                11

SEQ ID NO: 15           moltype = AA  length = 5
FEATURE                 Location/Qualifiers
source                  1..5
                        mol_type = protein
                        organism = synthetic construct
SEQUENCE: 15
QRNFY                                                       5
```

We claim:

1. An adjuvanted protein vaccine comprising: a non-phospholipid liposome and one or more proteins, wherein the protein is encapsulated within the non-phospholipid liposome, and wherein the one or more proteins comprise SEQ ID NO: 3.

2. The adjuvanted protein vaccine of claim 1, wherein the protein generates IgG antibody responses for 120 days after two injections of the adjuvanted protein vaccine, by subcutaneous or intramuscular routes.

3. The adjuvanted protein vaccine of claim 1, wherein the vaccine facilitates generation of IgG antibodies to spike proteins from multiple SARS-COV-2 variants.

4. The adjuvanted protein vaccine of claim 1, wherein the non-phospholipid liposome comprises: one or more poly-oxyethylene fatty acid ethers, one or more membrane stabilizing agents, one or more negative charge producing agents, and Vitamin E.

5. A modified spike protein sequence comprising SEQ ID NO: 3.

6. A method for generating an immune response in a subject, comprising administering the adjuvanted protein vaccine according to claim 1 to the subject.

7. The method of claim 6, wherein the adjuvanted protein vaccine is administered subcutaneously or intramuscularly.

8. The method of claim 6, wherein the method generates an IgG immune response.

9. The method of claim 6, wherein the method increases the immune response to SARS-COV-2 spike protein.

10. The method of claim 6, wherein the adjuvanted protein vaccine generates IgG antibody responses for 120 days after two injections of the adjuvanted protein vaccine, by subcutaneous or intramuscular routes.

\* \* \* \* \*